United States Patent [19]
Patchett et al.

[11] Patent Number: 5,925,659
[45] Date of Patent: Jul. 20, 1999

[54] ANTIBACTERIAL AGENTS

[75] Inventors: Arthur A. Patchett, Westfield; Ravi Nargund, East Brunswick; Meng-Hsin Chen; H. Russell Onishi, both of Westfield, all of N.J.

[73] Assignee: Merck & Co., Inc., Rahway, N.J.

[21] Appl. No.: 08/845,291

[22] Filed: Apr. 25, 1997

Related U.S. Application Data

[60] Provisional application No. 60/016,789, May 7, 1996.
[51] Int. Cl.$^6$ ................................................ A61K 43/76
[52] U.S. Cl. ..................... 514/374; 514/340; 514/342; 514/365; 548/200; 548/239
[58] Field of Search ............................ 514/374; 548/239

[56] References Cited

U.S. PATENT DOCUMENTS

| | | | |
|---|---|---|---|
| 2,714,082 | 7/1955 | Davies et al. | 514/374 |
| 2,772,281 | 11/1956 | Holly et al. | 548/239 |
| 2,840,565 | 6/1958 | Holly et al. | 548/239 |
| 3,681,496 | 8/1972 | Junghahnel et al. | 514/365 |
| 3,709,992 | 1/1973 | Schmeling et al. | 514/365 |
| 4,061,749 | 12/1977 | Powell | 544/53 |
| 4,565,654 | 1/1986 | Miller | 548/239 |
| 5,302,643 | 4/1994 | Millner et al. | |

OTHER PUBLICATIONS

M. Sako and Y. Maki, *Chem. Pharm. Bull.* 26(4) pp. 1236–1239 (1978).

*Primary Examiner*—Donald G. Daus
*Attorney, Agent, or Firm*—Sylvia A. Ayler; Richard R. Billups; Mark R. Daniel

[57] ABSTRACT

A compound represented by formula I:

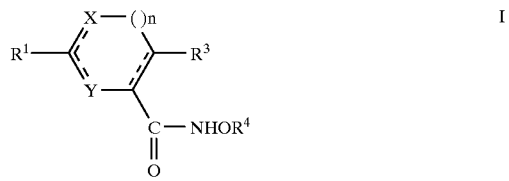

is disclosed. The compounds are active primarily against gram negative organisms. Pharmaceutical compositions and methods of treatment are also disclosed.

18 Claims, No Drawings

ANTIBACTERIAL AGENTS

CROSS REFERENCE TO RELATED APPLICATIONS

This application is based upon provisional application No. 60/016,789, filed on May 7, 1996.

BACKGROUND OF THE INVENTION

Lipid A (endotoxin) is an essential component of the outer membranes of gram-negative bacteria. Genetic evidence has established that inhibition of its biosynthesis is lethal to gram-negative bacteria (Galloway, S. M.; Raetz, C. R. H. *J. Biol. Chem.* 1990, 265, 6394–6402; Kelly, T. M.; Stachula, S. A.; Raetz, C. R. H.; Anderson, M. S. *J. Biol. Chem.* 1993, 268, 19866–19874). Furthermore, blocking lipid A biosynthesis renders bacteria sensitive to other antibiotics which poorly penetrate gram-negative organisms with an intact outer membrane. The second step in lipid A biosynthesis involves the deacetylation of uridine diphosphate-3-0-[R-3-hydroxymyristoyl]-N-acetylglucosamine by UDP-3-0-[R-3-hydroxymyristoyl]-GlcNAc deacetylase. It is the object of this invention to describe inhibitors of this enzyme which have gram-negative antibacterial activity. Earlier attempts to block bacterial outer membrane biosynthesis at the ketodeoxyoctanoate ($K_{do}$) stage met with limited success (Hammond, S. M.; et al. *Nature* 1987, 327, 730–732; Goldman, R.; Kohlbrenner, W.; Lartey, P.; Pernet, A. *Nature* 1987 329, 162–164.) since $K_{do}$ analogs penetrate bacteria poorly and inhibition at this step is not rapidly lethal to bacteria.

This invention is directed to certain heterocyclic hydroxamate compounds which have the ability to inhibit UDP-3-0-[R-3-hydroxymyristoyl]-GlcNAc deacetylase and, thereby, have gram negative antibacterial activity. The compounds can be used to treat gram negative infections of man and of animals alone and in combination with other antibiotics.

It is a further object of this invention to describe procedures for the preparation of these compounds. Still further objects of this invention will be apparent from the specification.

SUMMARY OF THE INVENTION

A compound represented by formula I:

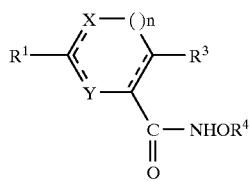

or a pharmaceutically acceptable salt thereof wherein:

$R^1$ represents $C_1$–$C_{12}$ alkyl, aryl $C_1$–$C_{12}$alkyl and aryl, wherein the alkyl group may be unsubstituted or substituted with 1–5 fluorines or 1–2 $OR^2$ groups, and aryl is selected from the group consisting of: phenyl, napthyl, indolyl, biphenyl, phenoxyphenyl, pyridyl, furanyl, thiophenyl and bithienyl, said aryl group being optionally substituted by 1–3 groups selected from $R^5$;

$R^2$ represents hydrogen, $C_1$–$C_6$ lower alkyl, phenyl or benzyl;

one of X and Y represents $N(R^2)_{0-1}$, and the other represents $N(R^2)_{0-1}$, O or S;

the dotted lines represent an optional bond;

$R^3$ represents H or $C_1$–$C_6$ lower alkyl optionally substituted by 1–3 groups selected from $OR^2$, $CO_2R^2$ or $N(R^2)_2$;

$R^4$ represents hydrogen, CO $C_1$–$C_6$ alkyl or CO phenyl and the alkyl and phenyl groups may be optionally substituted by 1–3 of $R^2$, $CO_2R^2$ and $N(R^2)_2$;

$R^5$ represents $C_1$–$C_6$ lower alkyl, $C_1$–$C_6$ lower alkoxy, halogen, trifluoromethyl, methylenedioxy, $N(R^2)_2$, $N(R^2)(COR^4)$, phenoxy, $CO_2R^2$, hydroxy, $SO_2R^2$, $CON(R^2)(R^2)$ $OCOR^4$ and aryl lower alkoxy wherein the phenoxy and aryl lower alkoxy groups may be substituted by 1–3 groups selected from $C_1$–$C_6$ lower alkyl, $C_1$–$C_6$ lower alkoxy, halogen, trifluoromethyl and hydroxy; and when no $R^5$ group is present, and $R^3$ represents H, the stereochemistry at the carbon atom bearing the group —C(O)—NHOR$^4$ is (R); and n represents 0 or 1.

Compositions and methods of treatment are also included.

DETAILED DESCRIPTION

In the above structural formula and throughout the instant specification, the following terms have the indicated meanings:

The alkyl groups specified above are intended to be of either a straight or branched configuration, and when two or more carbon atoms are present they may include a double or a triple bond. Examples of such alkyl groups are methyl, isopropyl, tertiary butyl, allyl, propargyl and the like.

Alkoxy groups include alkoxy groups of the specified length in either a straight or branched configuration and if two or more carbon atoms in length, they may include a double or triple bond. Examples of such alkoxy groups are methoxy, propoxy, allyloxy, propargyloxy and the like.

Methylenedioxy refers to a group which forms a ring fused to an aromatic ring through adjacent carbon atoms.

The term halogen is intended to include the halogen atoms fluorine, chlorine, bromine and iodine.

The term aryl within the present invention, unless otherwise specified, is intended to include phenyl, napthyl, indolyl, biphenyl, phenoxyphenyl, bithienyl, pyridyl, thiophenyl and furanyl.

Preferred compounds of the instant invention include those of Formula Ia:

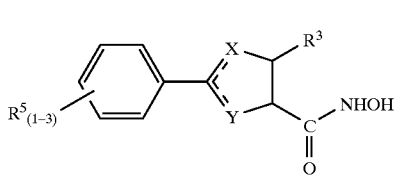

wherein:

one of X and Y represent $N(R^2)_{0-1}$, and the other represents $N(R^2)_{0-1}$, O or S;

$R^2$ represents hydrogen or $C_1$–$C_6$ lower alkyl;

dotted lines represent an optional bond;

$R^3$ represents H or $C_1$–$C_6$ lower alkyl optionally substituted by $OR^2$, $CO_2R^2$ or $N(R^2)(R^2)$;

$R^5$ represents $C_1$–$C_6$ lower alkyl, $C_1$–$C_6$ lower alkoxy, halogen, trifluoromethyl, methylenedioxy, $N(R^2)_2$, phenoxy, $CO_2R^2$, hydroxy, $R^2SO_2$, $CON(R^2)_2$ and benzyloxy wherein the phenoxy and benzyloxy groups may be substituted by $C_1$–$C_6$ lower alkyl, $C_1$–$C_6$ lower alkoxy, halogen, trifluoromethyl and hydroxy;

and pharmaceutically acceptable salts and individual diastereomers thereof.

Still more preferred compounds of the instant invention include those of Formula Ib:

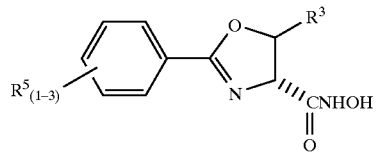

Ib wherein:

$R^3$ represents hydrogen or $C_1$–$C_6$ lower alkyl optionally substituted by $OR^2$ or $N(R^2)_2$;

$R^2$ represents hydrogen or $C_1$–$C_6$ lower alkyl;

$R^5$ represents $C_1$–$C_6$ lower alkyl, $C_1$–$C_6$ lower alkoxy, halogen, trifluoromethyl, methylenedioxy, phenoxy, hydroxy and benzyloxy, wherein the benzyloxy and phenoxy groups may be substituted by $C_1$–$C_6$ lower alkyl, $C_1$–$C_6$ lower alkoxy, halogen, trifluoromethyl and hydroxy groups; and the pharmaceutically acceptable salts and individual diastereomers thereof.

Specific compounds of the instant invention include:

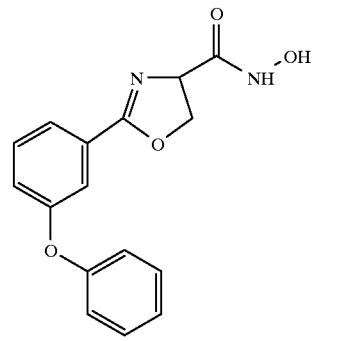

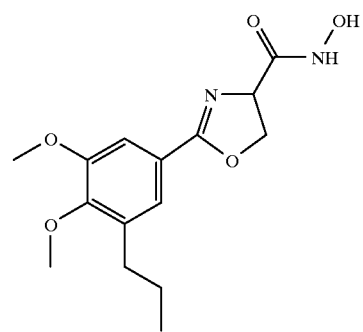

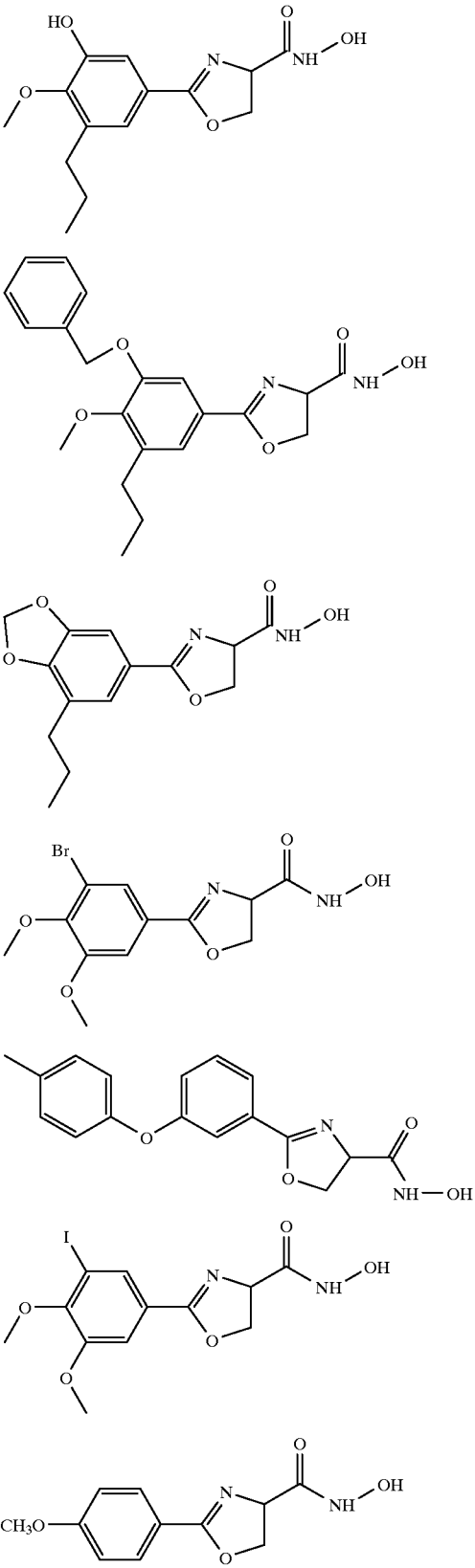

Representative examples of specific stereoisomers of the compounds are also included herein.

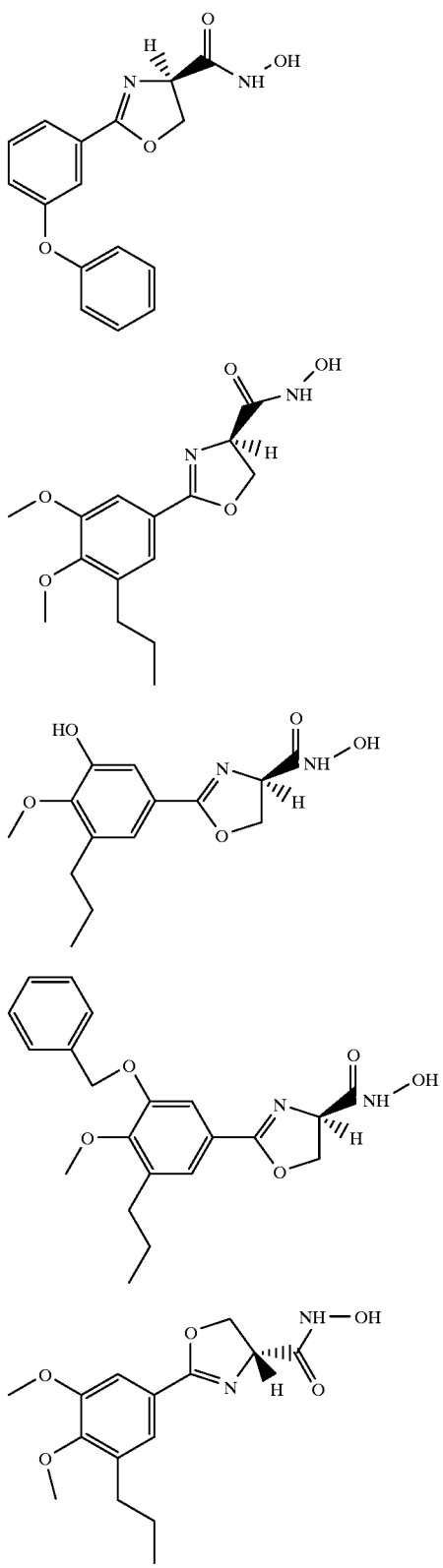

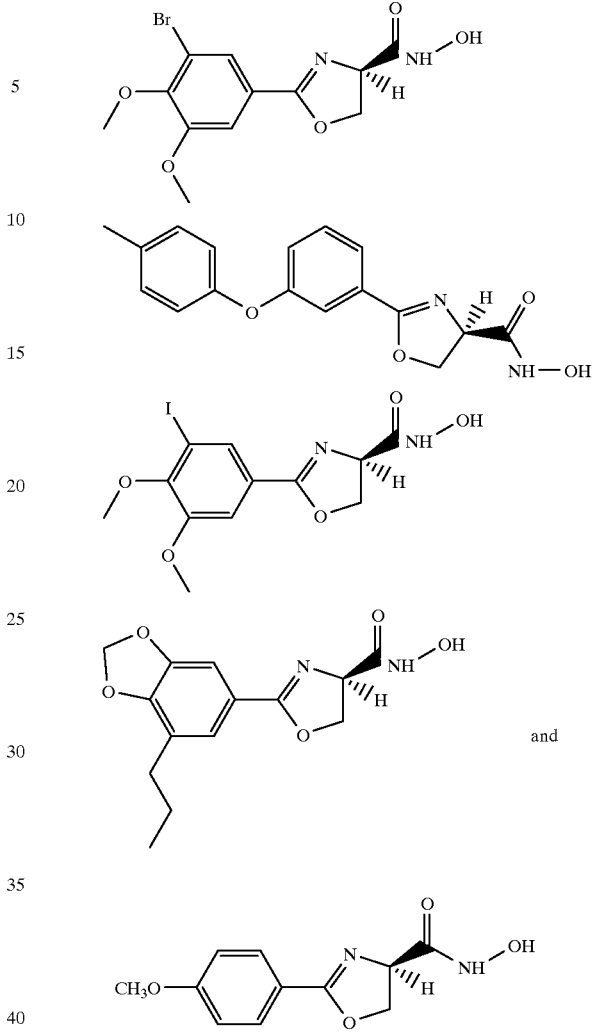

Pharmaceutically acceptable salts and individual diastereomers thereof are likewise included where not otherwise specified.

Throughout the instant application, the following abbreviations are used with the following meanings:

Bu: Butyl
Bn: Benzyl
BOC, Boc: t-butyloxycarbonyl
CBZ, Cbz: Benzyloxycarbonyl
DCC: Dicyclohexylcarbodimide
DMF: N,N-dimethylformamide
DMAP: 4-Dimethylaminopyridine
DMS: Dimethyl sulfide
DMSO: Dimethyl sulfoxide
EDC: 1-(3-dimethylaminopropyl)-3-ethylcarbodiimide hydrochloride
Et: ethyl
HOBT, HOBt: Hydroxybenztriazole
KHMDS: Potassium bis(trimethylsilyl) amide LAH: Lithium aluminum hydride
LHMDS: Potassium bis(trimethylsilyl)amide
Me: Methyl
Ms: Methanesulfonyl
Pd/C: 10% Palladium on Active Carbon
Pr: Propyl
TEA: Triethylamine
TFA: Trifluoroacetic acid
THF: Tetahydrofuran
TMS: Tetramethylsilane The compounds of the instant invention have an asymmetric center at the carbon atom to which the hydroxamate group is attached, which is preferred in the (R)-configuration. In general both (R)- and (S)-configurations of the carbon atom to which the $R^3$ group is attached are consistent with enzyme inhibition and antibacterial activity. Diastereomers arise when the $R^3$ group is present and their independent synthesis or chromatographic separations may be achieved as described herein. Their absolute stereochemistry may be determined by the x-ray crystallography of crystalline products or crystalline intermediates which are derivatized, if necessary, with a reagent containing a asymmetric center of known absolute configuration. All such isomers in pure form as well as in mixture, are included in the present invention.

The instant compounds are generally isolated in an unionized form. However, alkaline metal hydroxides and organic bases may be used to make salts of the hydroxamate group and of carboxylate and phenolic functionality which is present in some of the compounds of this invention. Pharmaceutically acceptable acid addition salts derived from inorganic and organic acids are also possible when basic amine functionality is present.

The preparation of compounds Formula I of the present invention may be carried out in sequential or convergent synthetic routes. Syntheses detailing the preparation of the compounds of Formula I in a sequential manner are presented in the following reaction schemes.

The phrase "standard peptide coupling reaction conditions" means coupling a carboxylic acid with an amine using an acid activating agent such as EDC and DCC in an inert solvent such as methylene chloride or chloroform in the presence of a coupling reagent such as HOBt. Acid chlorides and mixed anhydrides, which are either commercially available or prepared by standard procedures may be reacted with amines under peptide-type coupling conditions The uses of protective groups for amines and carboxylic acids to facilitate the desired reaction and minimize undesired ones are well documented. Conditions required to remove protecting groups which may be present can be found in Greene, T, and Wuts, P. G. W., *Protective Groups in Organic Synthesis*, John Wiley & Sons, Inc., New York N.Y. (1991). For example, removal of Bn group of O—Bn can be achieved by a number of methods known in the art, including catalytic hydrogenation with hydrogen in the presence of a noble metal or its oxide such as palladium on activated carbon in a protic solvent such as ethanol. The skills required in carrying out the reactions and purifications of the products are known to those skilled in the art. Purification procedures include crystallization and normal phase or reverse phase chromatography.

In Scheme 1, the heterocycle can be formed by reacting an imino ester of formula I with carboxyl protected amino acids of formula 2, wherein Y can be O, S or NH. Some imino esters of formula 1 are commercially available. Others can be prepared following literature methods. A widely used method involves the treatment of alkyl, aryl and heterocyclic nitrites with anhydrous HCl(g) in alcohols or in aprotic solvents like dioxane, THF and ether containing alcoholic solvents such as ethanol or methanol. The nitrile precursors for the synthesis of intermediates of formula 1, wherein $R^1$ may be as defined within the ambit of this invention, may by prepared by known methods. For a review that describes the synthesis of imino esters see Neilson, in Patai, *The Chemistry of Amidines and Imidates*, PP. 385–489, John Wiley & Sons, New York, (1975). In a typical experimental protocol amino acid derivatives of formula 2, wherein L is $CH_3$, $CH_2CH_3$, Bn, and the like are reacted with 1 in a suitable solvent such as methylene chloride in presence of a base such as triethylamine to give intermediates of formula 3.

There is considerable literature precedent for synthesis of oxazolines and thiazolines using the above method. For example, Elliott, D. F. (*J. Chem. Soc.* 1949, 589) have utilized the synthesis of oxazolines from imino ester and serine derivatives. Elliott, D. F., et al (*J. Chem. Soc.,* 1956, 4066) also described the formation of thiazoline rings from imino esters and cysteine derivatives.

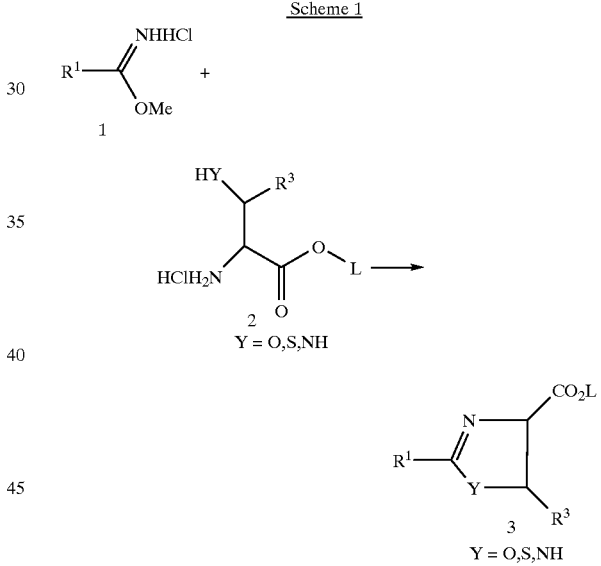

Scheme 1

Other applicable routes for the synthesis of oxazolines of formula 6, wherein $R^3$ includes substituents within the ambit of this invention, will be apparent from the specification.

Illustrated in Scheme 2 is a general method in which the heterocycle is elaborated by intramolecular cyclization of serine or threonine derivatives of formula 5 in presence of thionyl chloride.

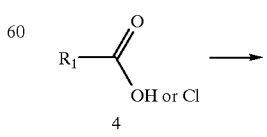

Scheme 2

-continued

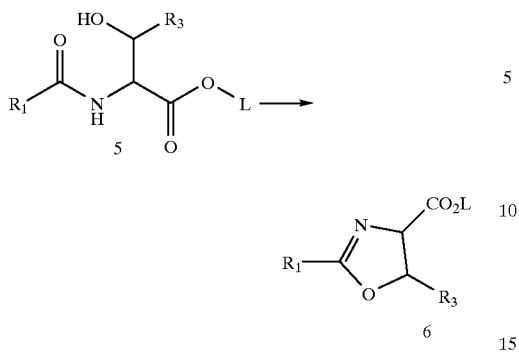

Intermediates of formula 5 can be prepared by standard peptide-type coupling of acids of formula 4 with protected amino acids (L=protecting group) of formula 2. Alternatively the acylation reaction can also be carried out by reacting acid chlorides of formula 4 with protected amino acids of formula 2 in an inert solvent like dichloromethane in the presence of triethylamine. Once again, many acids and acid chlorides of formula 4, wherein $R^1$ is defined within the ambit of this invention, are either commercially available or prepared by methods that are familiar to those skilled in the art.

Schemes 3–6 present some of the methods that are available to transform heterocyclic esters of formula 7 to their corresponding hydroxamic acids.

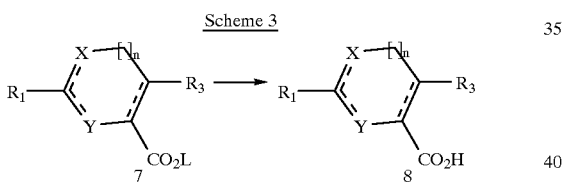

The methods that are presented in Schemes 3–6 are also useful to convert esters of formulas 3 and 6 to their respective hydroxamic acid derivatives. As shown in Scheme 3, ester 7 can be hydrolyzed to the corresponding carboxylic acid 8 by a number of standard methods. For example, removal of a benzyl group can be accomplished by reductive methods including hydrogenation in the presence of palladium catalyst in a protic solvent such as methanol. Methyl and ethyl esters can be hydrolyzed with lithium hydroxide in a protic solvent. An allyl ester can be cleaved with tetrakis-triphenylphosphine palladium catalyst in the presence of 2-ethylhexanoic acid in a variety of solvents.

As shown in Scheme 4, protected hydroxamic acids of formula 9 may be prepared by coupling acids of formula 8 with $NH_2O$—Bn under standard peptide coupling reaction conditions. Removal of the Bn group from 9 can be accomplished by catalytic hydrogenation using palladium on activated carbon to afford compounds of Formula I.

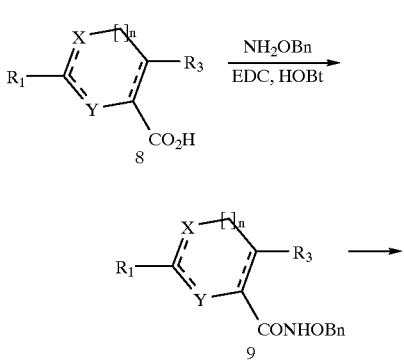

Compounds of Formula I may also be prepared as described in Scheme 5 and 6.

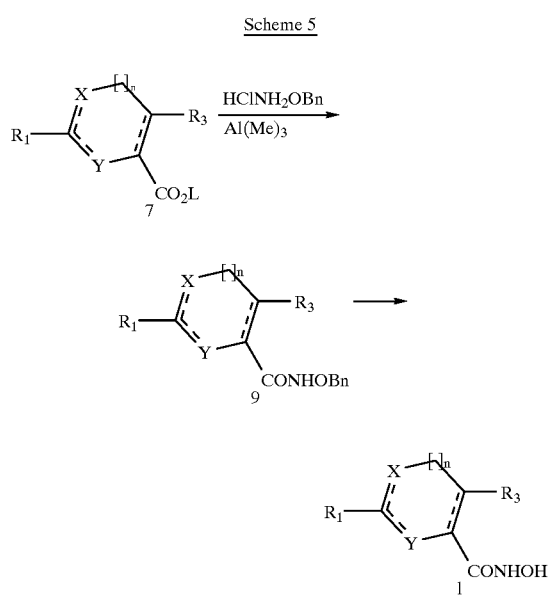

Ester 7 can be directly converted to N-benzyloxy amides of formula 9 by the method of Weinreb et al. (*Syn. Comm.,* 1982, 12, 989). In this procedure esters of formula 7 are converted to amides 9 by reacting it with the aluminum amide that is prepared from the reaction of trimethyl aluminum with O-benzyl hydroxylamine hydrochloride. Removal of the Bn group in Formula 9 by catalytic hydrogenation of palladium on activated carbon affords the compound of Formula I.

Other applicable routes for the synthesis of compounds Formula I of the present invention include a one-step transformation of esters of formula 7 to their hydroxamic acid derivatives by reaction with hydroxylamine (prepared from hydroxyamine HCl and sodium methoxide in methanol) and a catalytic amount of a base such as sodium methoxide in a protic solvent like methanol. Detailed experimental methods analogous to the one described in Scheme 6 are presented in Kierstead, R. W., Faraone, A., Goldberg, M. W. *J. Med. Chem.* 1963, 6, 77.

Scheme 6

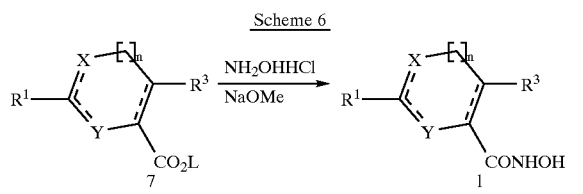

Compounds of Formula 13, wherein $R^4$ is as defined within the ambit of this invention may prepared as shown in Scheme 7, by reacting compounds of formula 9 with reagents such as 10, 11 and 12, wherein X is a good leaving group such as Cl, Br, I or an imidazole, in an inert solvent such as DMF.

Scheme 7

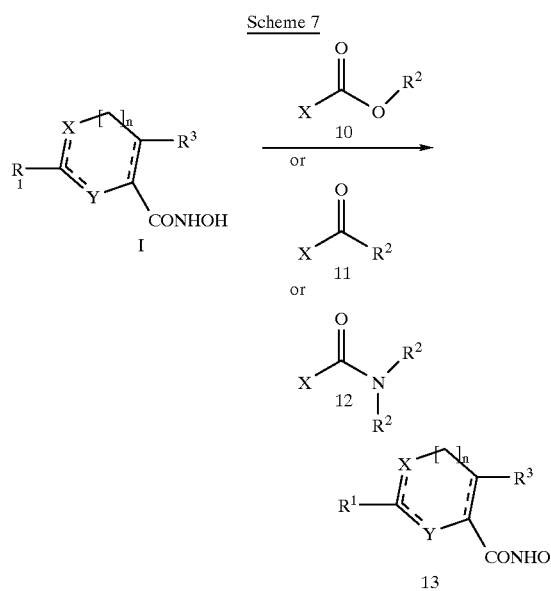

Other compounds of formula I, wherein n=0 and the heterocycles containing X and Y are oxazole, thiazole or imidazole, can be prepared by methods that are well documented in the literature. Heterocyclic esters of formula 7 can be synthesized by standard synthetic protocols and elaborated to their hydroxamic acid derivatives by taking advantage of methods documented in Schemes 3–6. For example, Knight, D. W., Rippon, D. E., and Pattenden, G. (*Synlett*, 1990, 1, 36) have used a 2,4-disubstituted oxazoline intermediate of formula 14 to synthesize 2,4-disubstituted oxazole 15 by carrying out the oxidation with nickel peroxide in cyclohexane as shown in Scheme 8.

Scheme 8

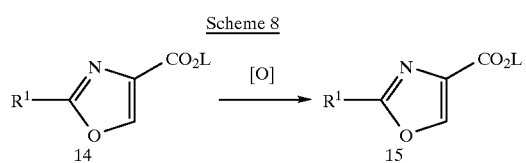

Compounds of formula 16, wherein Y may be O, S or NH, can be prepared by taking advantage of the chemical methods described in Schemes 1–7 but by using protected amino acids of formula 17.

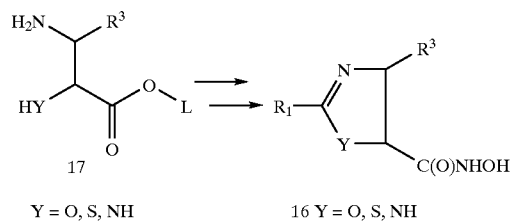

Y = O, S, NH      16 Y = O, S, NH

It is noted that in some cases the order of carrying out the foregoing reaction schemes may be varied to facilitate the reaction or to avoid unwanted products. The invention is further illustrated in connection with the following non-limiting examples.

EXAMPLE 1

E-1

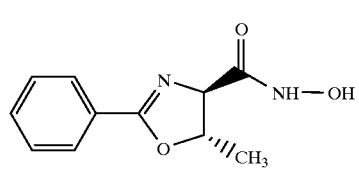

To a solution of (D)-threonine benzyl ester trifluoroacetate (3.65 mmol) in 10 mL of chloroform was added 0.51 mL of triethylamine followed by 1.18 g (3.65 mmol) of methylbenzimidate hydrochloride and stirred at ambient temperature for 18 h. The reaction was diluted with 10 mL of dry ether and the precipitate was filtered and washed with an additional 5 mL of ether. The filtrate was concentrated and the residue was chromatographed on 50 g of silica gel. Elution with hexane-ethylacetate (10:1) gave 0.696 g of the oxazoline product. This material was treated with 1.3 mL of a 0.67M solution of MeAlNHOBn in toluene (prepared according to the method of Weinreb et al. *Synth. Comm.* 1982, 12, 989) at 50° C. for 10 min.

The reaction mixture cooled to room temperature and quenched with 1 mL of 2N aqueous sodium hydroxide solution. The reaction mixture was diluted with 5 mL of water and extracted with ethyl acetate. The combined organics were washed with water (5 mL), brine (5 mL), dried over anhydrous potassium carbonate and concentrated. Flash chromatography over 10 g of silica gel (hexane-ethyl acetate 4:1) as the eluent gave 67 mg of the desired product.

This material was dissolved in 5 mL of methanol and 15 mg of 10% Pd/C and hydrogenated by using a balloon for 1 h. The catalyst was filtered off through a pad of celite and the filtrate was concentrated to give the title compound as a white solid.

Alternatively, the hydrogenolysis reaction can be accomplished with 20% Pd(OH)₂/C in methanol with the aid of a hydrogen balloon.

¹H NMR (400 MHz, CD₃OD) δ7.88 (d, 2H), 7.48 (d, 1H), 7.40 (t, 2H), 5.00 (dt, 1H), 4.48 (d, 1H), 1.50 (d, 3H).

EXAMPLE 2

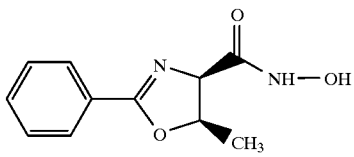

E-2

To 1.58 g (9.32 mmol) of (D)-serine methyl ester hydrochloride in 10 mL of a 1:1 mixture of dioxane-water at 0° C. was added 3.3 mL of triethylamine and 1.2 mL of benzoyl chloride and stirred for 1 h. the reaction mixture was diluted with 15 mL of ethyl acetate and 15 mL of water and extracted with 2×15 mL of ethyl acetate. The combined organics were washed with 5% hydrochloric acid (15 mL), brine (15 mL), dried over magnesium sulfate and concentrated to yield 1.69 g of the benzamide as a thick oil.

Thionyl chloride (3 mL) was added to 1.32 g of the benzamide compound and maintained at −100° C. overnight. The excess thionyl chloride was removed under reduced pressure and the residue was dissolved in 15 mL of chloroform and poured into a stirring solution of 50 mL of 10% aqueous sodium carbonate solution. The aqueous layer was separated and extracted with 3×15 mL of chloroform. The combined organics were washed with brine (50 mL), dried over magnesium sulfate, filtered and concentrated to give the oxazoline methyl ester (1.29 g) as a thick oil. This material was elaborated to the target compound as described in Example 1.

¹H NMR (400 MHz, CD₃OD) δ7.88 (d, 2H), 7.50 (d, 1H), 7.46 (t, 2H), 5.10 (dt, 1H), 5.00 (d, 1H), 1.40 (d, 3H).

EXAMPLE 3

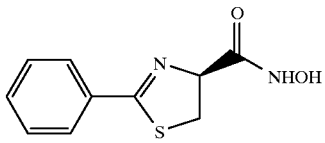

E-3

Step A

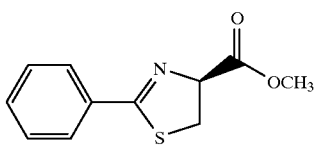

This material was synthesized from (D)-cysteine methyl ester hydrochloride (3.65 mmol) and methylbenzimidate hydrochloride as described in Example R1.

¹H NMR (400 MHz, CDCl₃) δ7.85 (d, 2H), 7.50–7.30 (m, 3H), 5.25 (dt, 1H), 3.80 (s, 3H), 3.75–3.50 (m, 2H).

Step B

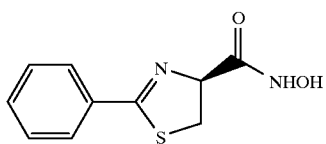

To a solution of 0.193 g of the intermediate from Step A in 2 mL of methanol was added a mixture of 62 mg of hydroxylamine hydrochloride and 0.25 mL of triethylamine in 0.25 mL of water and 1 mL of methanol. The reaction was vigourously stirred and kept in the freezer overnight. The reaction mixture was acidified with dilute aqueous acetic acid and the precipitate that formed was filtered and dried. NMR analysis indicated that this material was the desired product.

¹H NMR (400 MHz, CD₃OD) δ7.90 (d, 2H), 7.50 (d, 1H), 7.48 (t, 2H), 5.15 (dt, 1H), 3.80–3.55 (m, 2H).

EXAMPLE 4

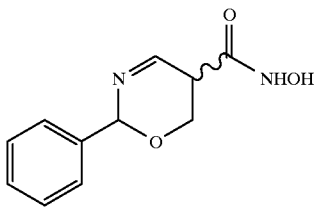

E-4

This material was synthesized by taking advantage of chemistry as described in Example 1.

¹H NMR (400 MHz, CD₃OD) δ7.95 (d, 2H), 7.48 (t, 1H), 7.40–7.30 (m, 1H), 4.55–4.38 (m, 2H), 4.20 (q, 1H), 2.34 (dt, 1H), 2.05 (dt, 1H).

EXAMPLE 5

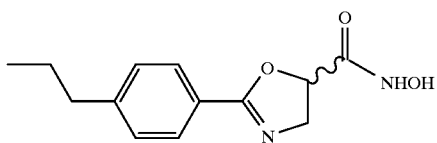

E-5

Step A

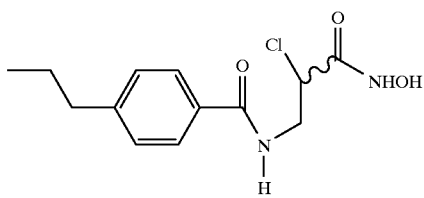

To a solution of 0.99 g of (D,L) isoserine methyl ester hydrochloride in 10 mL of a 1:1 mixture of dioxane-water at 0° C. was added 3.6 g of sodium bicarbonate and 1.51 mL of p-(n-propyl) benzoyl chloride and stirred for 1 h. The reaction mixture was poured into 20 mL of water and extracted with ethyl acetate (3×20 mL). The combined organics were washed with 5% aqueous hydrochloric acid (20 mL), brine (20 mL), dried over magnesium sulfate and concentrated to give 1.09 g of a crude product. This material was triturated with 1:1 mixture of hexane-ether to give the benzamide as a solid. This material was treated with 4 mL of thionyl chloride overnight. The excess thionyl chloride was removed under reduced pressure and the residue was taken up in 20 mL of chloroform and washed with 10 mL of 10% aqueous sodium carbonate solution. The organic layer was dried over magnesium sulfate, filtered and concentrated to give the chloride.

$^1$H NMR (400 MHz, CDCl$_3$) δ7.65 (d, 2H), 6.65 (bt, 1H), 4.38 (q, 1H), 3.90–3.80 (m, 2H), 3.77 (s, 3H), 2.60 (t, 2H), 1.62 (dt, 2H), 0.95 (t, 3H).

Step B

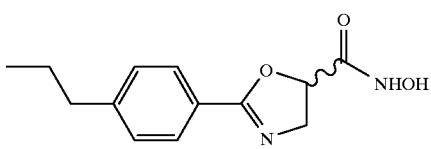

To a solution of 0.26 g of the intermediate from Step A in 4 mL of dry tetrahydrofuran at −78° C. was added 1.84 mL of a 0.5M solution of potassium bis(trimethylsilyl)amide in toluene and stirred for 10 min. The reaction was quenched with 5 mL of brine and extracted with 2×10 mL of ethyl acetate. The combined organics were dried over MgSO$_4$, filtered and concentrated to give the oxazoline methyl ester that was elaborated to the title compounds as shown in Example R-1.

$^1$H NMR (400 MHz, CD$_3$OD) δ7.88 (d, 2H), 7.29 (d, 1H), 5.10 (dd, 1H), 4.30 (dd, 1H), 4.16 (dd, 1H), 2.65 (t, 2H), 1.68 (dt, 2H), 0.96 (t, 3H).

EXAMPLE 6

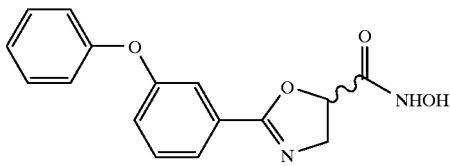

E-6

Prepared as described in Example 5 but by using 3-phenoxybenzoyl chloride in place of p-(n-propyl)benzoyl chloride.

$^1$H NMR (400 MHz, CD$_3$OD) δ7.75–7.30 (m, 5H), 7.15 (dd, 1H), 7.00 (dd, 1H), 5.10 (dd, 1H), 4.40–4.05 (m, 2H).

EXAMPLE 7

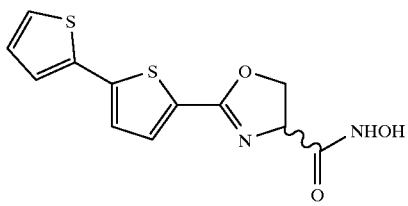

E-7

Step A

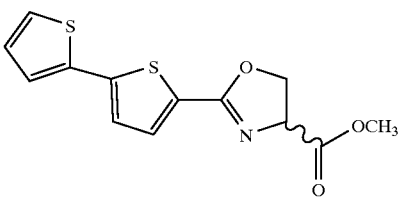

To a solution of 0.12 g of (DL)-serine methyl ester hydrochloride was added 0.14 g of 2-(thiophen-5-yl) thiophenyl acid, 0.23 g of EDC and 0.12 g of triethylamine and stirred at room temperature for 18 h. The reaction mixture was worked up under standard conditions and the crude product was subject to cyclization by using the thionyl chloride method of Example 2 to give the desired material (64 mg).

Step B

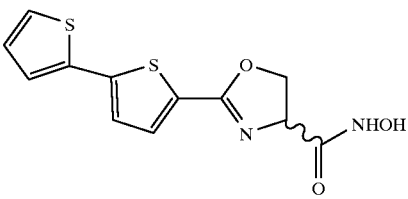

To 16 mg of hydroxylamine hydrochloride in 2 mL of dry methanol at 0° C. was added 0.10 mL of 25% sodium methoxide in methanol followed by the ester intermediate from Step A (64 mg). After 10 min. the reaction mixture was quenched with the addition of ice and the reaction mixture was acidified to pH=7 with acetic acid. The precipitate that formed was filtered and dried to produce the target compound.

$^1$H NMR (400 MHz, CD$_3$OD) δ7.60 (d, 1H), 7.43 (d, 1H), 7.35 (d, 1H), 7.23 (d, 1H), 7.09 (dd, 1H), 4.73 (dd, 1H), 4.66 (dd, 1H), 4.60 (dd, 1H).

EXAMPLE 8

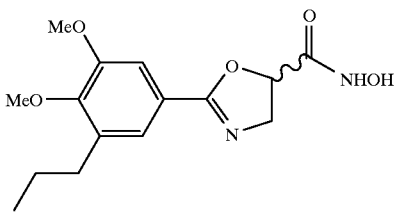

E-8

The oxazoline methyl ester was prepared from isoserine methyl ester hydrochloride and methyl [(3,4-dimethoxy)-5-n-propyl]benzoyl chloride (prepared as described in Step C of Example 7) as described in Example 5 and converted to the hydroxamic acid as described in Example 7 Step B.

$^1$H NMR (400 MHz, CD$_3$OD) δ7.50 (bs, 2H), 5.14 (t, 1H), 4.40–4.10 (m, 2H), 3.85 (s, 3H), 3.81 (s, 3H), 2.60 (t, 2H), 1.65 (q, 2H), 0.97 (t, 3H).

EXAMPLE 9

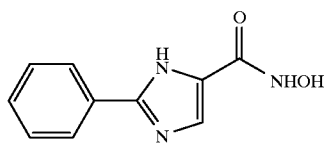
E-9

Step A

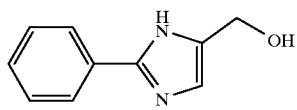

A solution of methylbenzimidate hydrochloride and 1,3-dihydroxyacetone was stirred in methanolic ammonia at 60° C. in a pressure bomb for 16 h. The reaction mixture was concentrated and the residue was taken up in chloroform and washed with water and brine, dried over MgSO$_4$, filtered and concentrated. The desired material was isolated after flash chromatography.

Step B

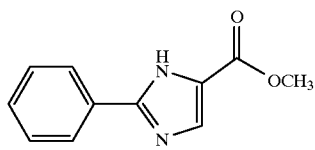

The imidazole alcohol (1.12 g) from Step B was dissolved in 50 mL of methanol and oxidized to the aldehyde with 5 g of activated manganese diioxide. After 18 h the solids were filtered off through a pad of celite. The filtrate was concentrated and the residue and 3.2 g of sodium cyanide were dissolved in 50 mL of methanol and 0.70 mL of glacial acetic acid and treated with activated manganese dioxide overnight. The solids were filtered off through a pad of celite and the filtrate was concentrated. The residue was taken up in 50 mL of water and extracted with 3×50 mL of dichloromethane. The organics was washed with saturated aqueous NaHCO$_3$ solution, dried over MgSO$_4$ and concentrated. Flash chromatography of the residue over 50 g of silica gel with CH2Cl2-acetone (1:1) as the eluent gave 0.569 g of product.

$^1$H NMR (400 MHz, CDCl$_3$) δ8.00–7.90 (d, 2H), 7.75 (s, 1H), 7.50–7.30 (m, 3H), 3.84 (s, 3H).

Step C

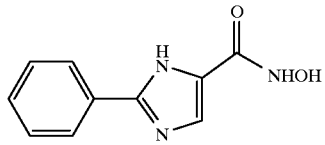

The intermediate from Step A was converted to the target compound using the procedure described in Example 1.

$^1$H NMR (400 MHz, CD$_3$OD) δ7.90 (d, 2H), 7.70 (s, 1H), 7.48–7.36 (m, 3H).

EXAMPLE 10

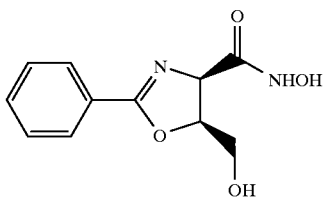
E-10

Step A

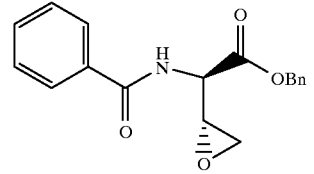

To a solution of 0.40 g of N-t-Boc-D-vinylglycine benzyl ester in 2 mL of dichloromethane was added 2 mL of trifluoroacetic at 0° C. and stirred for 1 h. The solvent was removed under reduced pressure and the residue was azeotroped with benzene. The residue was dissolved in 2 mL of water, 2 mL of dioxane and treated with 0.78 mL of triethylamine and 0.48 mL of benzoyl chloride. The reaction was stirred for 30 min. at 0° C. and poured into 10 mL of ethyl acetate and washed with 15 mL of 5% aqueous HCl, 5 mL saturated aqueous NaHCO$_3$, dried over MgSO$_4$ and concentrated. Flash chromatography over 5 g of silica gel with hexane-ethyl acetate (4:1) as the eluent gave 0.33 g of the benzamide. To a solution of this material in 3 mL of hexanes was added 0.73 g of mCPBA (80%) and stirred overnight. The reaction was quenched with 5 mL of saturated sodium bisulfite solution and extracted with ethyl acetate (2×25 mL). The combined organics were washed with saturated aqueous NaHCO$_3$ solution, dried over MgSO$_4$ and concentrated Flash chromatography (10 g silica gel) with hexane-ethyl acetate (4:1) as the eluent gave 0.216 g of the epoxide together with its diastereomer as a 4:1 mixture.

$^1$H NMR (400 MHz, CDCl$_3$) δ7.78 (d, 2H), 7.52 (d, 2H), 7.42 (t, 1H), 7.40–7.30 (s, 5H), 6.60 (d, 1H), 5.25 (dd, 1H), 3.60 (ddd, 1H), 2.80 (dd, 1H), 2.63 (dd, 1H).

Step B

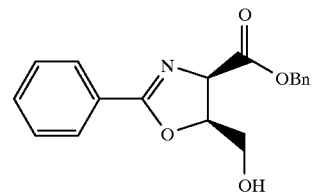

To a solution of the intermediate from Step A in 5 mL of dry toluene at −78° C. was added 0.090 mL of boron trifluoride etherate and the reaction was allowed to warm up to 0° C. and quenched with 5 mL of saturated aqueous NaHCO$_3$ solution and extracted with 3×10 mL of EtOAc. The combined organics were dried over MgSO$_4$, filtered and concentrated to give the desired material as a white solid.

Step C

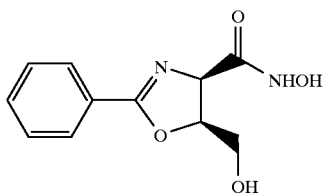

The intermediate from Step B was converted to the title compound by using chemistry detailed in Example R-1.

$^1$H NMR (400 MHz, CD$_3$OD) δ7.99 (d, 2H), 7.60–7.30 (m, 3H), 4.60 (d, 1H), 4.50–4.40 (m, 1H), 4.00–3.50 (m, 2H).

EXAMPLE 11

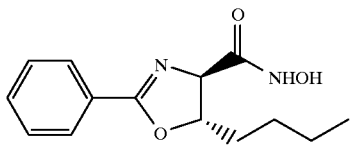

E-11

Step A

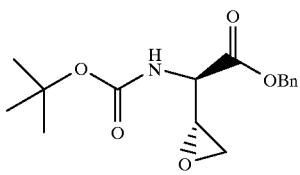

The N-t-Boc-D-vinylglycine benzyl ester of Example 10, Step A was replaced with N-t-Boc-D-vinylglycine methyl ester and the procedure run to produce the target compound.

Step B

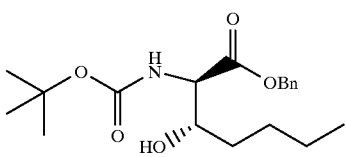

To a suspension of 27 mg of cuprous cyanide in 5 mL of dry THF at −78° C. was added 0.31 mL of a 2.0M solution of n-propylmagnesium chloride in ether and stirred for 1 h. A solution of 76 mg of the epoxide intermediate prepared in Step A in 2 mL of THF was added and stirred for 1 h. The reaction was allowed to warm up to 0° C. and quenched with 5 mL of saturated aqueous ammonium chloride solution. The reaction mixture was diluted with brine and extracted with ethyl acetate (3×5 mL). The combined organics were dried over MgSO$_4$, filtered and concentrated to provide a residue that was chromatographed on 10 g of silica gel. Elution with hexane-ethyl acetate (5:1) gave 33 mg of the desired product as an oil.

Step C

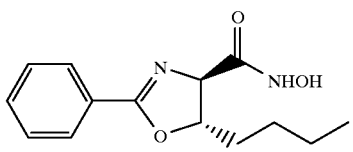

The Boc protecting group from the intermediate from Step B was removed with TFA and the corresponding amino alcohol was elaborated to the final product using the procedure of Example 1.

$^1$H NMR (400 MHz, CD$_3$OD) δ7.95(d, 2H), 7.55 (t, 1H), 7.45 (t, 2H), 5.50 (d, 1H), 4.80 (dt, 1H), 1.90–1.75 (m, 2H), 1.60–1.30 (m, 4H), 0.96 (t, 3H).

EXAMPLE 12

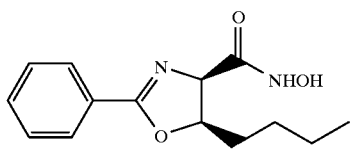

E-12

Step A

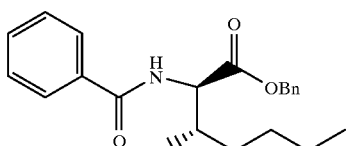

The Boc protecting group from the intermediate prepared in Step B of Example 11 was removed and the amino group was acylated with benzoyl chloride as described previously to give the desired benzamide.

Step B

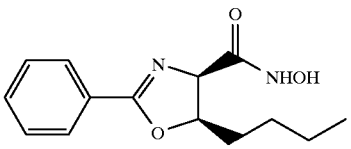

The intermediate from Step A was elaborated to the title compound by taking advantage of the thionyl chloride method to form the oxazoline and hydroxamic acid formation from the ester as described in Example 1.

$^1$H NMR (400 MHz, CD$_3$OD) δ7.95(d, 2H), 7.55 (t, 1H), 7.45 (t, 2H), 4.81 (q, 1H), 4.31 (d, 1H), 1.90–1.75 (m, 2H), 1.60–1.30 (m, 4H), 0.96 (t, 3H).

EXAMPLE 13

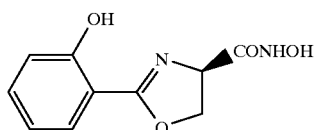

E-13

Step A

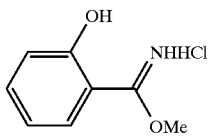

To a solution of o-cyanophenol (5.0 g) in 1/1 mixture of the methanol (5 ml) and ethyl ether (5 ml) there was bubbled HCl gas at 0° C. for 1 hour. The mixture was stored at −20° C. for 16 hours and then additional ethyl ether (50 ml) was added. The resulting mixture was recooled to −20° C. and the solid which came out was filtered off to give the desired hydroxybenzimidate HCl salt (4.6 g).

$^1$H NMR (300 MHz, CD$_3$OD): 7.95 (dd, 7 Hz, 1 Hz, 1H), 7.64 (m, 1H), 7.10 (d, 7 Hz, 1H), 7.08 (dt, 7 Hz, 1 Hz, 1H), 4.32 (s, 3H).

Step B

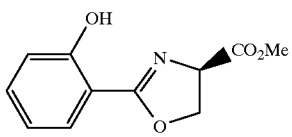

To (D)-serine methyl ester HCl salt (500 mg) as a suspension in chloroform (10 ml), was added methyl benzimidate HCl (586 mg) and TEA (0.4 ml). The mixture was refluxed for 20 hours and quenched with 0.5N HCl$_{aq}$. The mixture was extracted with ethyl acetate, then washed with water and brine. The organic layer was dried over sodium sulfate and concentrated. Purification by flash chromatography (hexanes/ethyl acetate=2/1) gave 371 mg of the title compound.

Step C

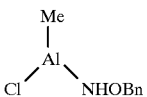

To a suspension of benzoxyamine HCl salt (317 mg) in toluene (2 ml) at 5° C. was slowly added a 2M solution (1 ml) of trimethylaluminum in toluene. After the addition was complete, the reaction mixture was allowed to warm to room temperature and stirred for 1 hour until the evolution of gas had ceased.

Step D

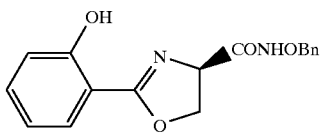

To a solution of the intermediate (361 mg) obtained from Step B in toluene (5 ml) was added the intermediate (6 ml) obtained from Step C and this mixture was then heated to 50° C. until no starting ester was observed by TLC. The mixture was cooled to room temperature and quenched with water. It was stirred for 30 minutes to form a white cloudy solution which was filtered through Celite. The filtrate was concentrated and purified by chromatatron (hexanes/ethyl acetate=2/1) to give the desired product.

Step E

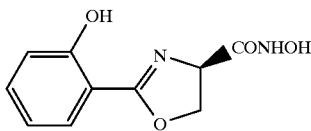

To a solution of the intermediate from Step E in methanol (5 ml) there was added Pd(OH)$_2$/C and placed under hydrogen (1 atmosphere). After stirring for 1 hour, the mixture was filtered through Celite to remove the Pd waste. The filtrate was concentrated to give crude material. This crude product was purified by PLC (methylene chloride/methanol=10/1) to give the target compound (122 mg).

$^1$H NMR (300 MHz, CD$_3$OD): 7.66 (dd, 7 Hz, 1 Hz, 1H), 7.39 (t, 7 Hz, 1H), 6.94 (d, 7 Hz, 1H), 6.88 (t, 7 Hz, 1H), 4.85 (m 1H), 4.60 (d, 9 Hz, 2H).

FAB-MS calc. for C$_{10}$H$_{10}$N$_2$O$_4$: 222; Found 223 (M+H).

The additional intermediates shown in Table 1 were prepared according to the above procedures as exemplified in Example 13, Step A. The final compounds were prepared according to Example 13, Step B, C, D and E.

TABLE 1

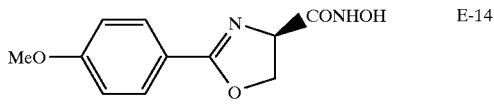

| entry | R | * stereocenter | product FAB-MS (M + H) |
|---|---|---|---|
| 1 | n-heptyl | R | C$_{11}$H$_{20}$N$_2$O$_3$ 229 |
| 2 | t-butyl | R | C$_8$H$_{14}$N$_2$O$_3$ 187 |
| 3 | m-tolyl | RS | C$_{11}$H$_{12}$N$_2$O$_3$ 221 |
| 4 | p-tolyl | RS | C$_{11}$H$_{12}$N$_2$O$_3$ 221 |

EXAMPLE 14

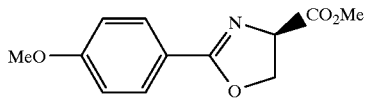

E-14

Step A

MeO—⟨phenyl⟩—oxazoline—CO$_2$Me

To a solution of (D)-serine methyl ester (5.04 g) in methylene chloride (150 ml) was added TEA (9 ml) and p-anisoyl chloride (5.0 g) at 0° C. The mixture was slowly warmed to room temperature and stirred an additional 12 hours and then quenched with 1N HCl$_{aq}$. The mixture was extracted with methylene chloride, then washed with water and brine. The organic layer was dried over sodium sulfate and concentrated. The residue was cooled to 0° C. and to it was added thionyl chloride (20 ml). The mixture was stored for 48 hours at 0° C. and then poured into cold $K_2CO_{3(aq)}$ solution slowly. It was extracted with methylene chloride, washed with water and brine. The organic layer was dried over sodium sulfate and concentrated to give the desired product (5.95 g).

Step B

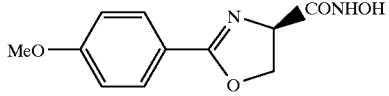

The target compound (2.1 g) was prepared from the intermediate obtained from Step A (5.95 g) according to the procedure described for Example 13, Step D and E.

$^1$H NMR (300 MHz, CD$_3$OD): 7.94 (d, 9 Hz, 2H)), 6.98 (d, 9 Hz, 2H), 4.71 (dd, 10 Hz, 8 Hz, 1H), 4.62 (dd, 10 Hz, 8 Hz, 1H), 4.54 (t, 8 Hz, 1H), (z, 1H), 3.84 (s, 3H).

FAB-MS calc. for $C_{11}H_{12}N_2O_4$: 236; Found 237 (M+H).

The additional final products shown in Table 2 were prepared according to Example 14, Step A and B from commercially available acid chlorides.

TABLE 2

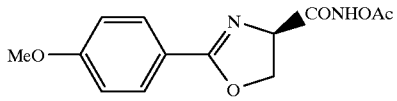

| entry | R | product FAB-MS (M + H) |
|---|---|---|
| 1 | o-tolyl | $C_{11}H_{12}N_2O_3$ 221 |
| 2 | 4-ethylphenyl | $C_{12}H_{14}N_2O_3$ 235 |
| 3 | 4-propylphenyl | $C_{13}H_{16}N_2O_3$ 249 |
| 4 | 4-biphenyl | $C_{16}H_{14}N_2O_3$ 283 |
| 5 | 3,4-dimethoxyphenyl | $C_{12}H_{14}N_2O_5$ 267 |
| 6 | 3,4,5-trimethoxyphenyl | $C_{13}H_{16}N_2O_6$ 297 |
| 7 | 2-furyl | $C_8H_8N_2O_4$ 197 |

EXAMPLE 15

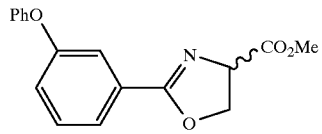

To a solution of compound (49 mg) from Example 14, Step B in DMF (2 ml) was added acetic anhydride (0.022 ml) and TEA (0.035 ml) at 0° C. The mixture was slowly warmed to room temperature and stirred an additional 12 hours and then poured into water. The mixture was extracted with ethyl ether, then washed with water and brine. The organic layer was dried over sodium sulfate and concentrated. The residue was purified by PLC (methylene chloride/methanol=95/5) to give the desired product (21 mg).

$^1$H NMR (300 MHz, CDCl$_3$): 7.83 (d, 9 Hz, 2H)), 6.84 (d, 9 Hz, 2H), 4.96 (dd, 10 Hz, 8 Hz, 1H), 4.70 (s, 1H), 4.67 (dd, 10 Hz, 8 Hz, 1H) 3.82 (s, 3H), 2.20 (s, 3H).

EXAMPLE 16

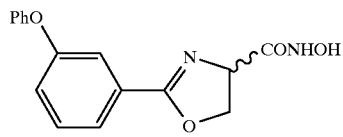

Step A

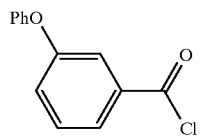

To a solution of 3-phenoxybenzoic acid (856 mg) in benzene (20 ml) then was added oxalyl chloride (0.38 ml) and a catalytic amount of DMF at 0° C. The mixture was stirred at 0° C. for 10 minutes and then warmed to room temperature for an hour. The mixture was concentrated to give the crude acid chloride.

Step B

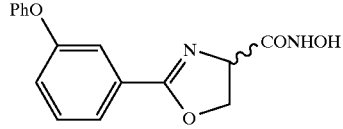

The title compound (513 mg) was prepared from the intermediate obtained from Step A according to the procedure described for Example 14, Step A.

Step C

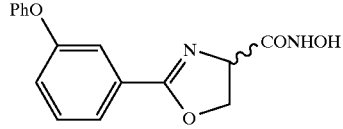

To a solution of hydroxylamine HCl (76 mg) in methanol (2 ml) was added sodium methoxide (0.25 ml, 25% in methanol) at 0° C. The resulting white cloudy solution was filtered through Celite and the filtrate was added to a solution of the intermediate (273 mg) obtained from Step B in methanol (1 ml). The mixture was cooled to 0° C. and another portion of sodium methoxide (0.21 ml, 25% in methanol) was added. This resulting solution was stored at 0° C. for 12 hours and then a portion of the solvent (~1.5 ml) was evaporated under vacuo. The residue was diluted with water (2 ml) and to it was added 2N HCl (0.5 ml). At this point the desired hydroxamic acid precipitated out. By filtering the thick suspension, the desired product was isolated as a pink solid. Recrystallization (methanol/ether) of this crude material gave a pale pink solid (165 mg).

$^1$H NMR (300 MHz, CD$_3$OD): 7.69 (d, 8 Hz, 1H), 7,53 (s, 1H), 7.44 (t, 8 Hz, 1H), 7.38 (t, 8 Hz, 2H)), 7.17 (m, 2H), 7.01 (d, 8 Hz, 2H), 4.75 (dd, 10 Hz, 8 Hz, 1H), 4.63 (t, 8 Hz, 1H), 4.56 (t, 8 Hz, 1H).

EI-MS calc. for $C_{16}H_{14}N_2O_4$: 298; Found 298.

EXAMPLE 17

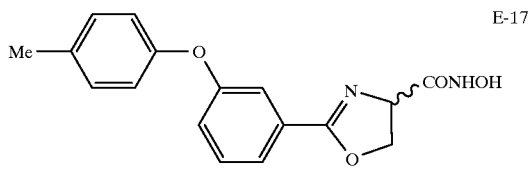

E-17

Step A

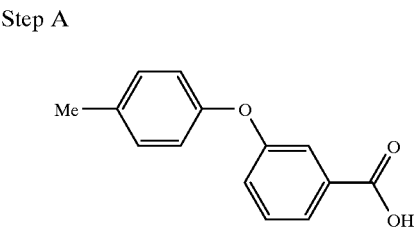

To a suspension of sodium hydride (160 mg) in pyridine (2.5 ml) was added methyl 3-hydroxybenzoate (608 mg) in pyridine (2.5 ml) at 0° C. After the addition was complete, the reaction mixture was allowed to warm to room temperature and stirred for 10 minutes until the evolution of gas had ceased and then cuprous bromide DMS (986 mg) was added. After stirring for 30 minutes, to the mixture was added 4-iodotoluene (1.3 g) in pyridine (2.5 ml) and the resultant mixture was refluxed for 18 hours. This mixture was then cooled to room temperature and poured into an aqueous solution of copper sulfate. It was extracted with ether, washed with copper sulfate solution, brine and dried over sodium sulfate. The solution was then filtered and concentrated. To a solution of resulting residue in methanol (5 ml) was added lithium hydroxide (500 mg) in water (3 ml) and the resultant solution was heated at reflux for an hour. The mixture was concentrated and the residue in 1N NaOH was extracted with hexanes and the organic layer was discarded. The aqueous layer was acidified with 1N HCl to pH~2.0 in an ice bath. At this time the desired carboxylic acid precipitated out. By filtering the suspension, the desired product was isolated (522 mg).

Step B

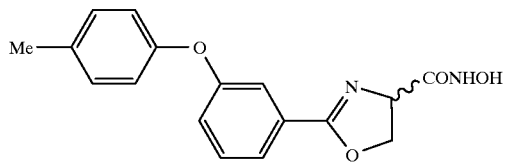

The title compound (460 mg) was prepared from the intermediate obtained from Step A (522 mg) according to the procedures described for Example 16, Step A, B and C.

$^1$H NMR (300 MHz, CD$_3$OD): 7.66 (d, 8 Hz, 1H), 7.49 (s, 1H), 7.41 (t, 8 Hz, 1H), 7.18 (m, 3H), 6.91 (d, 7 Hz, 2H), 4.74 (dd, 10 Hz, 8 Hz, 1H), 4.63 (dd, 10 Hz, 8 Hz, 1H), 4.55 (t, 8 Hz, 1H), 2.33 (s, 3H).

EI-MS calc. for C$_{17}$H$_{16}$N$_2$O$_4$: 312; Found 312.

EXAMPLE 18

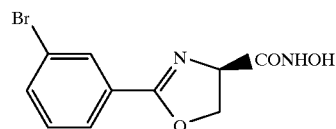

E-18

Step A

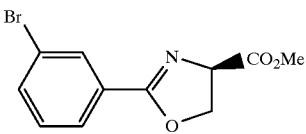

The synthesis intermediate was prepared by the procedure described in Example 14, Step A, from 3-bromobenzoyl chloride (1 ml), (D)-serine methyl ester (1.17 g), TEA (2.6 ml) and thionyl chloride (5 ml). Purification by flash chromatography (hexanes/ethyl acetate=4/1) gave the title compound 1.32 g.

Step B

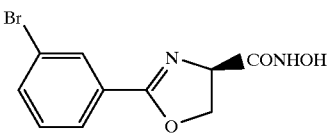

The synthesis intermediate was prepared by the procedure described in Example 16, Step C, from the intermediate (284 mg) prepared in the Step A, hydroxylamine HCl (84 mg), and two portions of sodium methoxide (0.27 ml and 0.23 ml, 25% in methanol). Recrystallization (twice from methanol) of crude material gave pure solid (138 mg).

$^1$H NMR (300 MHz, CD$_3$OD): 8.12 (s, 1H), 7.92 (d, 7 Hz, 1H), 7.71 (d, 7 Hz, 1H), 7.39 (t, 7 Hz, 1H), 4.79 (dd, 10 Hz, 8 Hz, 1H), 4.67 (dd, 10 Hz, 8 Hz, 1H), 4.59 (t, 8 Hz, 1H).

FAB-MS calc. for C$_{10}$H$_9$N$_2$O$_3$: 285; Found 285, 287.

EXAMPLE 19

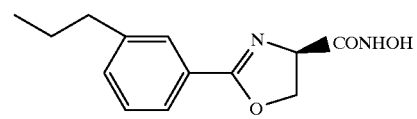

E-19

Step A

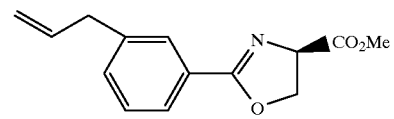

To a solution of the intermediate (320 mg) from Example 18, Step A, in toluene (5 ml) was added Pd(PPh$_3$)$_4$ (32 mg) and allyltributyltin (0.38 ml) and this mixture was heated to 110° C. for 12 hours. The mixture was concentrated in vacuo and purified by flash chromatography (hexanes/ethyl acetate=3/1) to give the desired product (140 mg).

Step B

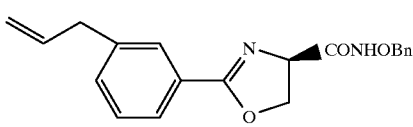

The synthesis intermediate was prepared by the procedure described in Example 13, Step D, from the intermediate (134 mg) prepared in the Step A and the intermediate (1.2 ml) prepared in Example 13, Step C. Purification by flash chromatography (hexanes/ethyl acetate=2/1) gave the title compound (120 mg).

Step C

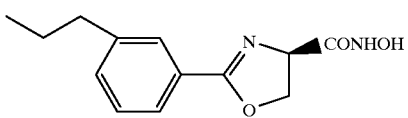

This final product prepared by the procedure described in Example 13, Step E, from the intermediate (120 mg) prepared in the Step B. Recrystallization (methanol/ methylene chloride) of crude material gave pure solid (61 mg).

$^1$H NMR (300 MHz, CD$_3$OD): 7.79 (m, 2H), 7.37 (m, 1H), 4.75 (dd, 10 Hz, 8 Hz, 1H), 4.65 (dd, 10 Hz, 8 Hz, 1H), 4.57 (t, 8 Hz, 1H), 2.63 (t, 7 Hz, 2H), 1.65 (m, 2H), 0.93 (t, 7 Hz, 3H).

FAB-MS calc. for C$_{13}$H$_{16}$N$_2$O$_3$: 248; Found 249.

EXAMPLE 20

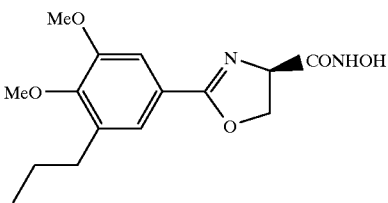

E-20

Step A

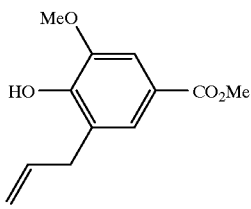

To a solution of methyl 4-hydroxy-3-methoxybenzoate (4.55 g) in DMF (100 ml) was added K$_2$CO$_3$ powder (5.17 g) and allyl bromide (2.6 ml). After 1 hour, the mixture was poured into water and extracted with ether. The organic layer was washed with water, brine, and dried over sodium sulfate. The organic solvent was removed under vacuo to give crude material (5.45 g). A solution of this crude material (4.22 g) in diethylaniline (15 ml) was heated at 200° C. for 10 hours to complete the rearrangement. The mixture was cooled to room temperature and poured into a 3N HCl aqueous solution and then extracted with ether. The organic layer was washed with water, brine, and dried over sodium sulfate. The organic solvent was removed under vacuo to give the rearrangement product (4.1 g).

Step B

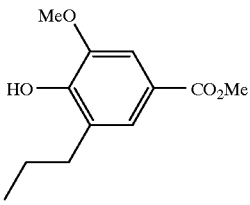

To a solution of the intermediate (1.44 g) from Step A in methanol (15 ml) was added Pd/C and placed under hydrogen (1 atmosphere). The reaction was monitor by TLC. After stirring for 1 hour, the reaction was complete and the mixture was filtered through Celite to move the Pd waste. The filtrate was concentrated to give the desired intermediate (1.42 g).

Step C

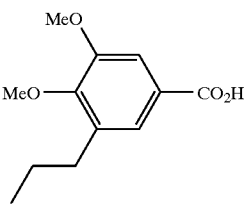

To a solution of the intermediate (436 mg) from Step B in DMF (10 ml) was added K$_2$CO$_3$ powder (538 mg) and methyl iodide (0.13 ml). After 1 hour, the mixture was poured into water and extracted with ether. The organic layer was washed with water, brine, and dried over sodium sulfate. The organic solvent was removed under vacuo to give crude material (464 mg). To this crude material (451 mg) in methanol (10 ml) was added lithium hydroxide (240 mg) in water (5 ml). After stirring 16 hours at room temperature, the mixture was diluted with water. The aqueous mixture was extracted with methylene chloride and the organic layer was discarded. The aqueous layer was acidified with 1N HCl in an ice bath to give a cloudy solution. By filtering the suspension, the desired carboxylic acid was isolated (422 mg).

Step D

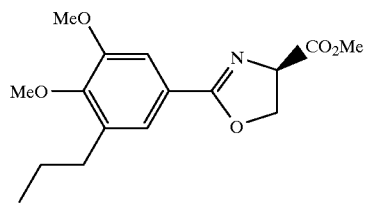

To a solution of the intermediate (422 mg) obtained in Step C was added (D)-serine methyl ester (439 mg), EDC (721 mg), HOBt (576 mg) and N-methylmorpholine (0.31 ml). The mixture was stirred at room temperature for 16 hours. The solution was then diluted with ethyl ether and washed with saturated sodium bicarbonate followed by brine. The organic layer was dried over sodium sulfate and concentrated. Purification by MPLC (hexanes/ethyl acetate= 1/1) gave the coupling product (611 mg). The coupling product (458 mg) was cooled to 0° C. and to it was added thionyl chloride (5 ml). The mixture was stored for 16 hours at 0° C. and then poured into a cold K₂CO₃(aq) solution slowly. The mixture was extracted with methylene chloride, washed with water and brine. The organic layer was dried over sodium sulfate and concentrated. Purification by MPLC (hexanes/ethyl acetate=1/1) to give the desired product (432 mg).

Step E

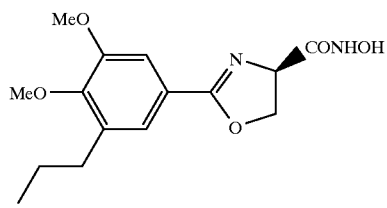

The title compound (100 mg) was prepared from the intermediate obtained from Step D (176 mg) according to the procedure described for Example 13, Step D and E.

$^1$H NMR (300 MHz, CD$_3$OD): 7.46 (d, 2H)z, 1H), 7.40 (d, 2H)z, 1H), 4.74 (dd, 10 Hz, 8 Hz, 1H), 4.64 (dd, 10 Hz, 8 Hz, 1H), 4.58 (t, 8 Hz, 1H), 3.88 (s, 3H), 3.83 (s, 3H), 2.60 (t, 7 Hz, 2H), 1.60 (m, 2H), 0.94 (t, 7 Hz, 3H).

EXAMPLE 21

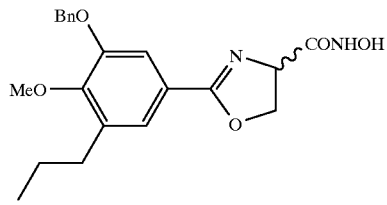

E-21

Step A

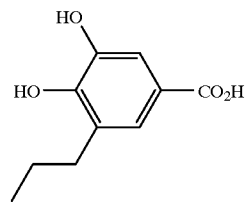

To a solution of the intermediate (667 mg) from Example 20, Step C in methylene chloride (20 ml) was added boron tribromide (3.58 ml, 1N in methylene chloride) at −78° C. After stirring 1 hour at −78° C., the mixture was warmed up to room temperature and stirred for another hour. At this time the reaction was not complete. The mixture was re-cooled to −78° C. and another portion of boron tribromide (2.68 ml) was added. The reaction was slowly warmed up to room temperature and stirred for another 60 hours. The mixture was quenched with water and extracted with ethyl acetate. The organic layer was washed with brine, dried over sodium sulfate. Concentration under vacuo and purification by flash chromatography (methylene chloride/methanol=1/6) gave the desired product (491 mg).

Step B

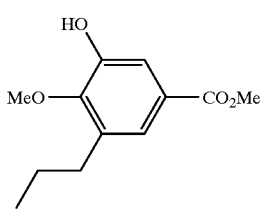

To a solution of the intermediate (491 mg) from Step A in DMF (10 ml) was added K₂CO₃ powder (692 mg) and methyl iodide (0.313 ml). After 16 hours, the mixture was poured into water and extracted with ether. The organic layer was washed with water, brine, and dried over sodium sulfate. Concentration and purification (MPLC, hexanes/ethyl acetate=4/1) gave the title compound (67 mg).

Step C

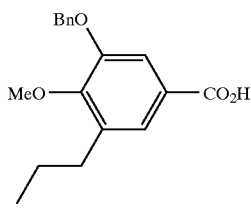

To a solution of the intermediate (67 mg) from Step B in DMF (1 ml) was added K₂CO₃ powder (82 mg) and benzyl bromide (0.04 ml). After 16 hours, the mixture was poured into water and extracted with ether. The organic layer was washed with water, brine, and dried over sodium sulfate. The organic solvent was removed under vacuo to give the crude product (82 mg). To a solution of crude residue in methanol (2 ml) was added lithium hydroxide (60 mg) in water (0.5 ml) and this mixture was heated at reflux for an hour. The mixture was concentrated. The residue in 1N NaOH was extracted with hexanes and the organic layer was discarded. The aqueous layer was acidified with 1N HCl to pH~2.0 in an ice bath. At this time the desired carboxylic acid precipitated out. By filtering the suspension solution, the desired product was isolated (45 mg).

Step D

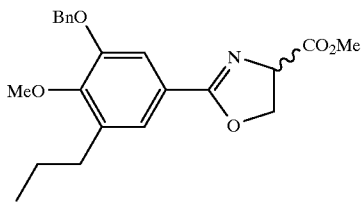

The synthesis intermediate was prepared by the procedure described in Example 16, Step A, from the intermediate from Step C (45 mg), and oxalyl chloride (0.012 ml) to give the corresponding acid chloride which was converted to the title compound (23 mg) by the procedure described in Example 14, Step A using (D,L)-serine methyl ester (21 mg), TEA (0.046 ml) and thionyl chloride (0.5 ml).

Step E

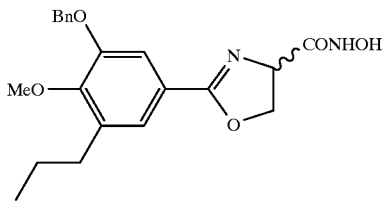

This product was prepared by the procedure described in Example 16, Step C, from the intermediate (23 mg) prepared in the Step D, hydroxylamine HCl (8.3 mg), and two portions of sodium methoxide (0.027 ml and 0.014 ml, 25% in methanol). Purification by PLC (methylene chloride/methanol=20/1) gave the title compound (7 mg) and recovered starting material (5 mg).

$^1$H NMR (300 MHz, CD$_3$OD): 7.55 (d, 2 Hz, 1H), 7.48 (d, 7 Hz, 2H), 7.43 (d, 2H)z, 1H), 7.38 (m, 2H), 7.33 (m, 1H), 5.14 (s, 3H), 4.74 (dd, 10 Hz, 2 Hz, 1H), 4.64 (t 8 Hz, 1H), 4.55 (t, 8 Hz, 1H), 3.86 (s, 3H), 2.62 (t, 7 Hz, 2H), 1.61 (m, 2H), 0.95 (t, 7 Hz, 3H).

EI-MS calc. for C$_{21}$H$_{24}$N$_2$O$_5$: 384; Found 384.

EXAMPLE 22

E-22

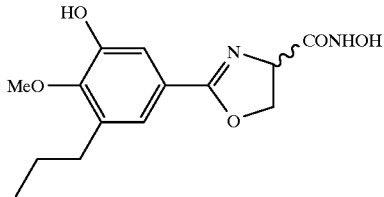

To a solution of the intermediate (5 mg) obtained from Example 21, Step E in methanol (1 ml) was added Pd/C and placed under hydrogen (1 atmosphere). After stirring 1 hour, the mixture was filtered through Celite to remove the Pd waste. The filtrate was concentrated to give the target compound (3.2 mg).

$^1$H NMR (300 MHz, CD$_3$OD): 7.30 (d, 2H)z, 1H), 7.27 (d, 2Hz, 1H), 4.72 (dd, 10 Hz, 2Hz, 1H), 4.68 (t 8 Hz, 1H), 4.57 (t, 8 Hz, 1H), 3.82 (s, 3H), 2.60 (t, 7 Hz, 2H), 1.61 (m, 2H), 0.95 (t, 7 Hz, 3H).

EI-MS calc. for C$_{14}$H$_{18}$N$_2$O$_5$: 294; Found 294.

EXAMPLE 23

E-23

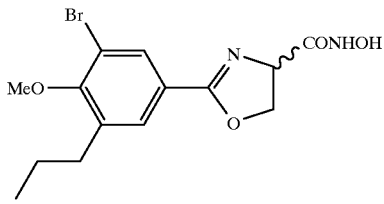

Step A

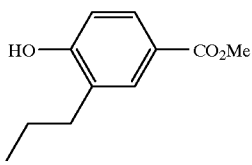

To a solution of methyl 4-hydroxybenzoate (12.16 g) in DMF (70 ml) was added K$_2$CO$_3$ powder (16.5 g) and allyl bromide (10.3 ml). After 1 hour, the mixture was poured into water and extracted with ether. The organic layer was washed with water, brine, and dried over sodium sulfate. The organic solvent was removed under vacuo to give crude material which was heated to reflux for 1 hours to complete the rearrangement. The mixture was cooled to room temperature and then purified by MPLC (hexanes/ethyl acetate= 8/1) to give the desired product (8.8 g).

Step B

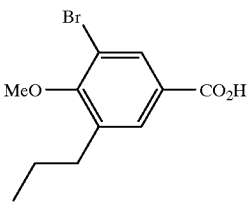

To a solution of bromine (1.2 ml) in chloroform (50 ml) was added sodium acetate (0.91 g) and this mixture was cooled to 0° C. To it was added the intermediate obtained from Step A (1.4 g) and the mixture was allowed to warm to room temperature. After 1 hour at room temperature, the mixture was poured into Na$_3$SO$_{3(aq)}$ and extracted with ether. The organic layer was washed with brine, dried over sodium sulfate and concentrated to give the desired product. To residue in DMF (30 ml) was added K$_2$CO$_3$ powder (1.98 g) and methyl iodide (0.89 ml), and it was stirred 16 hours. The mixture was then poured into water and extracted with ether, washed with water, brine, and dried over sodium sulfate. The resulting solution was concentrated and purified by MPLC to give desired benzoate (1.69 g). To this benzoate (0.57 g) in methanol (10 ml) was added lithium hydroxide (0.12 g) in water (1 ml). After stirring 3 hours at room temperature, the mixture was diluted with water. The aqueous mixture was extracted with methylene chloride and the organic layer was discarded. The aqueous layer was acidified with 1N HCl in an ice bath to give a thick suspension. By filtering the suspension, the desired carboxylic acid was isolated (0.512 g).

Step C

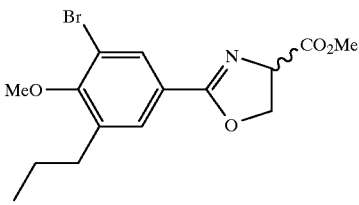

The synthesis intermediate was prepared by the procedure described in Example 16, Step A, from the intermediate from Step B (200 mg), and oxalyl chloride (0.14 ml) to give the corresponding acid chloride which was converted to the title compound by the procedure described in Example 14, Step A using (D,L)-serine methyl ester (171 mg), TEA (0.3 ml) and thionyl chloride (1 ml). Purification by PLC (hexanes/ethyl acetate=4/1) gave the desired product (170 mg).

Step D

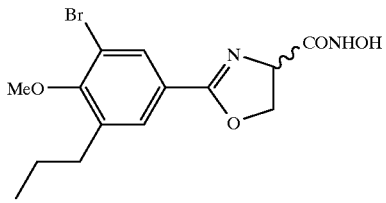

This product was prepared by the procedure described in Example 16, Step C, from the intermediate (170 mg) prepared in the Step C, hydroxylamine HCl (70 mg), and two portions of sodium methoxide (0.23 ml and 0.11 ml, 25% in methanol). Recrystallization (methanol/ethyl acetate) gave the title compound (85 mg).

$^1$H NMR (300 MHz, CD$_3$OD): 8.00 (d, 2Hz, 1H), 7.80 (d, 2 Hz, 1H), 4.80 (dd, 10 Hz, 2Hz, 1H), 4.73 (t, 8 Hz, 1H), 4.61 (t, 8 Hz, 1H), 3.85 (s, 3H), 2.68 (t, 7 Hz, 2H), 1.65 (m, 2H), 0.97 (t, 7 Hz, 3H).

EI-MS calc. for C$_{14}$H$_{17}$BrN$_2$O$_4$: 357; Found 356, 358.

EXAMPLE 24

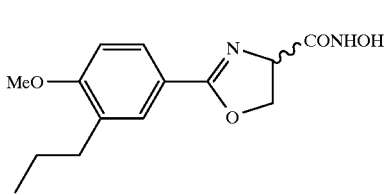

E-24

To a solution of the intermediate (20 mg) obtained from Example 23, Step D in methanol (2 ml) was added Pd/C and K$_2$CO$_3$ powder (8 mg) and placed under hydrogen (1 atmosphere). After stirring ½ hour, the mixture was filtered through Celite to remove the Pd and potassium salt wastes. The filtrate was concentrated to give the title compound (11 mg).

$^1$H NMR (300 MHz, CD$_3$OD): 7.79 (dd, 8 Hz, 2Hz, 1H), 7.73 (d, 2Hz, 1H), 6.98 (d, 8 Hz, 1H), 4.72–4.50 (m, 3H), 3.87 (s, 3H), 2.60 (t, 7 Hz, 2H), 1.60 (m, 2H), 0.93 (t, 7 Hz, 3H).

EI-MS calc. for C$_{14}$H$_{18}$N$_2$O$_5$: 278; Found 278.

EXAMPLE 25

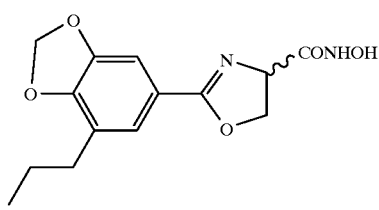

E-25

Step A

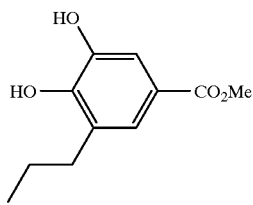

To a solution of the intermediate (716 mg) from Example 20, Step B in methylene chloride (20 ml) was added boron tribromide (9.8 ml, 1N in methylene chloride) at −78° C. It was then warmed up to room temperature and stirred for 60 hours. The mixture was quenched with water and extracted with ethyl acetate. The organic layer was washed with brine, and dried over sodium sulfate. Concentration under vacuo gave the dihydroxy carboxylic acid to which was added thionyl chloride (0.5 ml) in methanol (10 ml) and this solution was refluxed for ½ hour. The title compound was obtained after concentration under vacuo.

Step B

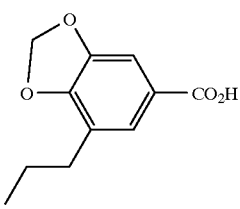

To a solution of the intermediate obtained from Step A in DMF (7 ml) was added KF (696 mg), and diiodomethane (0.19 ml) and it was then heated at 120° C. for 2 hours. After cooling down to room temperature, the mixture was poured into water, and extracted with ether. The organic layer was washed with water, brine and dried over magnesium sulfate. Concentration under vacuo and purification by flash chromatography (hexanes/ethyl acetate=5/1) gave the desired product. To methyl ester in methanol (5 ml) was added lithium hydroxide (252 mg) in water (1 ml) and the solution was heated to reflux. After ½ hour, the mixture was concentrated and diluted with water. The aqueous layer was acidified with 1N HCl in an ice bath to give thick suspension. By filtering the suspension, the desired carboxylic acid was isolated.

Step C

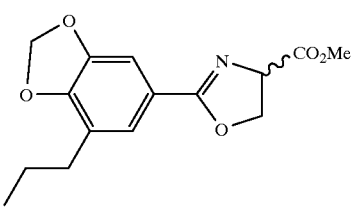

The synthesis intermediate was prepared by the procedure described in Example 16, Step A, from the intermediate from Step A, and oxalyl chloride (0.21 ml) to give the corresponding acid chloride which was converted to the title compound by the procedure described in Example 14, Step A using (D,L)-serine methyl ester (280 mg), TEA (0.67 ml) and thionyl chloride (2 ml).

Step D

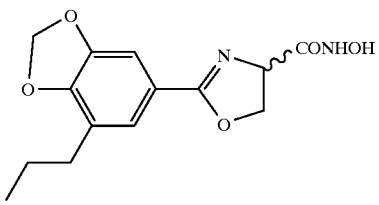

This product was prepared by the procedure described in Example 16, Step C, from the intermediate (83 mg) prepared in the Step C, hydroxylamine HCl (70 mg), and two portions of sodium methoxide (0.27 ml and 0.21 ml, 25% in methanol). Recrystallization (methanol/ethyl acetate hexanes) gave the target compound (220 mg).

$^1$H NMR (300 MHz, CD$_3$OD): 7.39 (d, 2Hz, 1H), 7.24 (d, 2Hz, 1H), 6.01 (s, 2H), 4.71 (dd, 10 Hz, 2Hz, 1H), 4.61 (dd, 8 Hz, 2Hz, 1H), 4.53 (t, 8 Hz, 1H), 2.58 (t, 7 Hz, 2H), 1.65 (m, 2H), 0.94 (t, 7 Hz, 3H).

EI-MS calc. for C$_{14}$H$_{16}$N$_2$O$_5$: 292; Found 292.

EXAMPLE 26

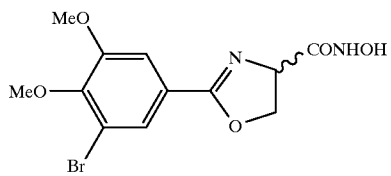

E-26

Step A

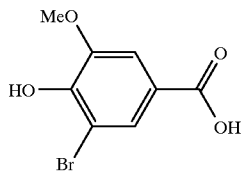

To a solution of 4-hydroxy-3-methoxybenzoic acid (1.68 g) in acetic acid (20 ml) was added bromine (1.76 g) in acetic acid (2 ml) at 20° C. This mixture was warmed to room temperature and stirred for ½ hour. The resulting mixture was poured into an ice-water solution and stirred for additional 20 minutes to give thick suspension. By filtering the suspension, the desired carboxylic acid was isolated (1.07 g).

Step B

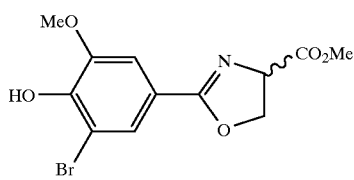

To a solution of the intermediate (1.07 g) obtained in Step A was added (D)-serine methyl ester (1.0 g), EDC (1.23 g), HOBt (511 mg) and TEA (0.9 ml). The mixture was stirred at room temperature for 60 hours. The solution was then diluted with ethyl ether and washed with saturated sodium bicarbonate followed by brine. The organic layer was then dried over sodium sulfate and concentrated. The coupling product was cooled to 0° C. and to it was added thionyl chloride (5 ml). The mixture was stored for 16 hours at 0° C. and then poured into cold K$_2$CO$_{3(aq)}$ solution slowly. The mixture was extracted with methylene chloride, washed with water and brine. The organic layer was dried over sodium sulfate and concentrated. Purification by PLC (hexanes/ethyl acetate=1/1) gave the desired product (300 mg).

Step C

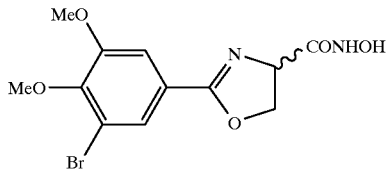

To a solution of the intermediate (300 mg) from Step B in DMF (3 ml) was added K$_2$CO$_3$ powder (196 mg) and methyl iodide (0.09 ml) and this mixture was heated to 60° C. After 1 hour, the mixture was poured into water and extracted with ether. The organic layer was washed with water, brine, and dried over sodium sulfate. Concentration under vacuo and purification by PLC (hexanes/ethyl acetate=1/1) gave the desired product (148 mg) which was converted to the title compound (89 mg) according to the procedure described for C-Example 5, Step C.

$^1$H NMR (300 MHz, CD$_3$OD): 7.72 (br. s, 1H), 7.59 (br. s, 1H), 4.73–4.56 (m, 3H), 3.90 (s, 3H), 3.85 (s, 3H).

EI-MS calc. for C$_{12}$H$_{13}$BrN$_2$O$_5$: 345; Found 344, 346.

EXAMPLE 27

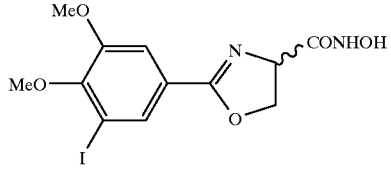

E-27

Step A

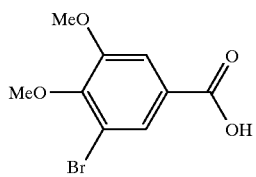

To a solution of the intermediate (450 mg) obtained from Example 26, Step A in DMF (10 ml) was added K$_2$CO$_3$ powder (0.7 g) and methyl iodide (0.34 ml), and it was stirred at 60° C. for 1 hour. The mixture was poured into water. The mixture was extracted with ether, washed with water, brine, and dried over sodium sulfate. The resulting solution was concentrated to give the desired benzoate which was dissolved in methanol (10 ml) and to it was added lithium hydroxide (0.3 g) in water (2 ml). After stirring 1 hour at room temperature, the mixture was concentrated. The residue was diluted with water and the aqueous mixture extracted with methylene chloride. The organic layer was discarded. The aqueous layer was acidified with 1N HCl in an ice bath to give thick suspension. By filtering the suspension, the desired carboxylic acid was isolated (0.44 g).

Step B

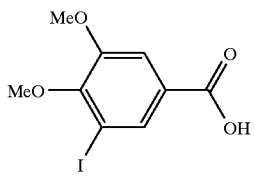

To an oil free sodium hydride (prepared from 60% in mineral oil, 100 mg) suspension in THF (10 ml) was slowly added the intermediate (440 mg) obtained from Step A in THF (5 ml). After 5 minutes, the mixture was cooled to −78° C. and then t-BuLi (3 ml, 1.7M in hexanes) was added. The mixture was stirred at −78° C. for several minutes and $I_2$ (642 mg) in THF (2 ml) was added slowly. The resulting mixture was stirred for 5 more minutes and poured into 0.5N HCl aqueous solution. The mixture was extracted with ether, washed with brine, and dried over sodium sulfate. After concentration, the desired product was isolated (250 mg).

Step C

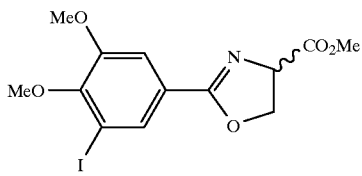

The synthesis intermediate was prepared by the procedure described in Example 16, Step A, from the intermediate from Step B, and oxalyl chloride (0.11 ml) to give the corresponding acid chloride which was converted to the title compound by the procedure described in Example 14, Step A using (D,L)-serine methyl ester (188 mg), TEA (0.34 ml) and thionyl chloride (2 ml).

Step D

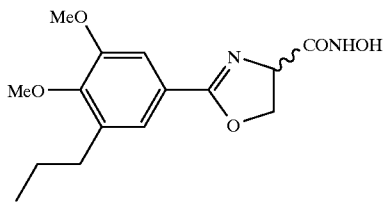

This product was prepared by the procedure described in Example 16, Step C, from the intermediate prepared in the Step C, hydroxylamine HCl (60 mg), and two portions of sodium methoxide (0.2 ml and 0.16 ml, 25% in methanol). Recrystallization (methanol) gave the target compound (240 mg).

$^1$H NMR (300 MHz, $CD_3OD$): 7.93 (d, 2 Hz, 1H), 7.61 (d, 2 Hz, 1H), 6.01 (s, 2H), 4.78–4.57 (m, 3H), 3.90 (s, 3H), 3.84 (s, 3H).

EXAMPLE 28

E-28

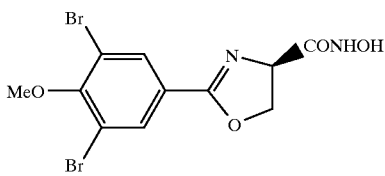

Step A

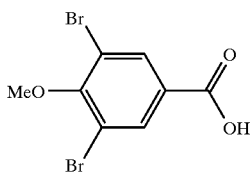

To a solution of bromine (3.2 ml) in chloroform (100 ml) was added sodium acetate (7.56 g) and this mixture was cooled to −78° C. To it was added methyl 4-hydroxybenzoate (4.56 g) and the mixture was allowed to warm to room temperature. After 1 hour at room temperature, the mixture was poured into $Na_3SO_{3(aq)}$ and extracted with ether. The organic layer was washed with brine, dried over sodium sulfate and concentrated to give 9.3 g of desired product. To residue (1.12 g) in DMF (10 ml) was added $K_2CO_3$ powder (1.49 g) and methyl iodide (0.45 ml) and the mixture was heated at 80° C. for 2 hours. The mixture was cooled down and poured into water. The mixture was extracted with ether, washed with water, brine, and dried over sodium sulfate. The resulting solution was concentrated to give crude material (1.01 g). To this crude material (0.9 g) in methanol (10 ml) was added lithium hydroxide (0.226 g) in water (2 ml). After stirring 2 hours at room temperature, the mixture was diluted with water. The aqueous mixture was extracted with methylene chloride and the organic layer was discarded. The aqueous layer was acidified with 1N HCl in an ice bath to give a thick suspension. By filtering the suspension, the desired carboxylic acid was isolated (0.85 g).

Step B

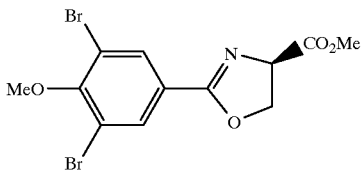

The synthesis intermediate was prepared by the procedure described in Example 16, Step A, from the intermediate from Step A (312 mg), and oxalyl chloride (0.096 ml) to give the corresponding acid chloride which was converted to the title compound (211 mg) by the procedure described in Example 14, Step A using (D,L)-serine methyl ester (171 mg), TEA (0.417 ml) and thionyl chloride (3 ml).

Step C

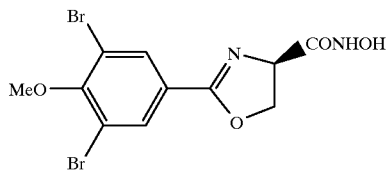

This product was prepared by the procedure described in Example 16, Step C, from the intermediate (170 mg) prepared in the Step B, hydroxylamine HCl (36 mg), and two portions of sodium methoxide (0.12 ml and 0.1 ml, 25% in methanol). Recrystallization (twice from methanol) of crude material gave pure solid (70 mg).

$^1$H NMR (300 MHz, CD$_3$OD): 8.16 (s, 2H), 4.79 (dd, 10 Hz, 2 Hz, 1H), 4.67 (dd, 10 Hz, 8 Hz, 1H), 4.59 (t, 8 Hz, 1H), 3.91 (s, 3H).

FAB-MS calc. for C$_{11}$H$_{10}$BrN$_2$O$_4$: 394; Found 393, 395, 397.

EXAMPLE 29

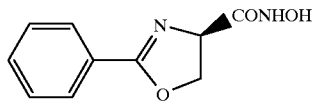

E-29

Step A

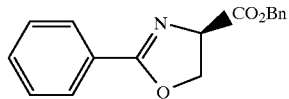

A solution of Boc-(D)-serine benzyl ester (1.1 g) in 1/1 mixture of the TFA and methylene chloride was stirred for 1 hour and then concentrated and azeotroped from toluene to give D-serine benzyl ester HCl salt. The residue was dissolved in methylene (15 ml), and added methyl benzimidate HCl (732 mg) and TEA (0.5 ml). The mixture was stirred at room temperature for 3 hours and then concentrated. Purification by flash chromatography (hexanes/ethyl acetate=6/1) gave 572 mg of the title compounds.

Step B

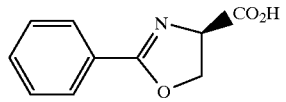

To a solution of 141 mg of the intermediate from Step A in methanol (5 ml) was added Pd/C and placed under hydrogen (1 atmosphere). After stirring for 1 hour, the mixture was filtered through Celite to remove the Pd waste. The filtrate was concentrated to give the title compound (97 mg).

Step C

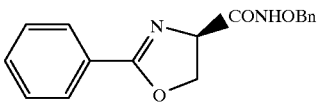

To a solution of 97 mg of the intermediate from Step B in a 3/10 mixture of the acetone and THF was added N-methylmorpholine and i-butyl chloroformate at −5° C. The mixture was stirred for 1 hour and to it was added benzyloxyamine (67 mg). The mixture was warmed to room temperature for 1 hour and then diluted with ethyl acetate and washed with water and brine. The organic layer was dried over sodium sulfate and concentrated. Purification by flash chromatography (hexanes/ethyl acetate=2/1) gave 75 mg of the title compound.

Step D

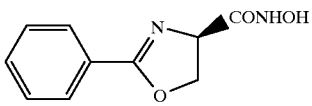

To a solution of 75 mg of the intermediate from Step C in methanol (5 ml) was added Pd(OH)$_2$/C and placed under hydrogen (1 atmosphere). After stirring for 1 hour, the mixture was filtered through Celite to remove the Pd waste. The filtrate was concentrated to give crude material. This crude product was recrystallized from methanol and ether to give the title compound (43 mg).

$^1$H NMR (300 MHz, CD$_3$OD): 7.97 (d, 7 Hz, 2H), 7.56 (t, 7 Hz, 1H), 7.47 (t, 7 Hz, 2H), 4.78 (dd, 10, 8 Hz, 1H), 4.67 (t, 8 Hz, 1H), 4.60 (dd, 10, 8 Hz).

The utility of the compounds of the present invention as antibacterial agents can be demonstrated by the methodology set forth below. Stock solutions of compounds were prepared by dissolving them in dimethylsulfoxide at 0.008 g/ml. For determination of MIC, 2-fold serial dilutions were prepared in Mueller-Hinton broth to yield 0.05 ml of antibiotic-containing medium per well. Inocula were prepared from cultures grown overnight in trypticase-soy broth at 37° C. Cell densities were adjusted to A$_{660}$=0.1, the OD standardized preparations were diluted 1:1000 in Mueller-Hinton broth, and wells were inoculated with 0.05 ml of the diluted bacteria giving a final cell density of approximately 1×10$^5$ colony forming units per ml. Microtiter plates were incubated at 37° C. for 18 h in a humidified incubator, and the MIC was recorded as the lowest drug concentration that inhibited visible growth.

Inhibition of UDP-3-0-[R-3-hydroxymyristoyl]-GlcNAc deacetylase was determined using a radiochemical assay in 40 mM bis-tris buffer, pH5.5 at 30° C. according to Kelly, T. M.; Stachula, S. A.; Raetz, C. R. H.; Anderson, M. S. *J. Biol. Chem*, 1993, 268, 19866–19874. The enzyme source was a membrane-free extract of *E. coli* strain JB1104 (Williamson, J. M.; Anderson, M. S.; Raetz, C. R. H. *J. Bacteriol.* 1991, 173, 3591–3596.

In comparison to known compounds, e.g., 4-carbohydroxamido-2-phenyl-2-oxazoline, disclosed in Stammer, et al. *J. Am. Chem. Soc.* 1956, 79: 3236–3240 the compounds of the invention are unexpectedly more potent against selected strains of *E. coli*. Moreover, the compounds of the invention are more potent inhibitors of UDP-3-0-[R-3-hydroxymyristoyl]-GlcNAc deacetylase than 4-carbohydroxamido-2-phenyl-2-oxazoline.

In addition, the compounds surprisingly enhance the antibacterial potency of antibiotics, such as macrolide antibiotics, e.g., azithromycin, clarithromycin and erythromycin, as well as other antibiotics, e.g., bacitracin and rifampicin. This can be demonstrated using the following procedure.

Compounds were tested for their effects on the activity of azithromycin, bacitracin and rifampicin against *E. coli* MB2884. Serial two-fold dilutions of the compounds were tested in a checker-board fashion. The checkerboard arrangement permitted the testing of many combinations of concentrations in each experiment. The combinations of compounds were inoculated with an equal volume of a $10^{-2}$ dilution of an overnight culture of MB2884 grown in Mueller-Hinton broth and adjusted to an optical density of 0.1 at a wavelength of 660 nm. The microtiter plates were incubated for 18 h at 37° C. and the wells were scored for turbidity. The inhibitory concentrations were converted to fractional inhibitory concentrations (FIC) and plotted. The shape of the resulting isobolograms were used to determine synergy (Sande, M. A., and G. L. Mandel. 1985. *The Pharmacological Basis of Therapeutics*, seventh edition. A. G. Gilman, L. S. Goodman, T. W. Rall, eds., MacMillan, N. Y., page 1085).

The compounds of Formula I can be administered to animals, including man, to treat gram negative bacterial infections. They may also be given along with other antibiotics, such as the macrolides, e.g., erythromycin, rifampicin and azithromycin, to achieve or enhance the gram negative antibacterial activity, or with other non-macrolide antibiotics to achieve or enhance the spectrum or potency of the particular antibacterial agent against gram negative organisms.

Likewise, the compounds of formula I can be used with other agents which are in and of themselves useful in conjunction with antibacterial agents. For example, bacterial cell wall permeabilizing agents can be included. Representative examples of such compounds include EDTA, polymixin B nonapeptide, poly-L-lysine and neomycin. Other permeability enhancing agents known to those skilled in the art can be included herein as well.

The compounds of this invention can be administered by oral, parenteral or topical routes of administration and can be formulated in dosage forms appropriate for each route of administration. Solid dosage forms for oral administration include capsules and tablets. In such forms, the active compound is admixed with at least one inert pharmaceutically acceptable carrier such as sucrose, lactose or starch and often a lubricating agent such as magnesium stearate is included. Capsules and tablets may also include buffering agents.

Liquid dosage forms for oral administration include pharmaceutically acceptable emulsions, solutions, suspensions, syrups, and elixirs containing inert diluents commonly used in the art, such as water. Besides such inert diluents, compositions can also include adjuvants, such as wetting agents, emulsifying and suspending agents, and sweetening, flavoring and perfuming agents. The oral compositions can also include one or more additional antibacterial agents, e.g., an antibiotic, such as a macrolide, for example, azithromycin, clarithromycin or erythromycin, a beta lactam antibiotic, such as the orally active penicillins or cephalosporins, a quinolone or fluoroquinolone, such as norfloxacin, ofloxacin or ciprofloxacin, antibacterial sulfonamides, such as sulfisoxazole and the combination product trimethoprim/sulfamethoxazole, as well as other antibiotics, e.g., rifampicin.

Preparations according to this invention for parenteral administration include, for example, sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use. The injectable form of the composition may also include another antibiotic/antibacterial compound, such as those noted above with respect to oral compositions, as well as antibiotics which are typically used as parenterals.

The specific examples provided herein are for purposes of illustration only, and are not intended to be limitations on the disclosed invention.

What is claimed is:

1. A compound represented by formula I:

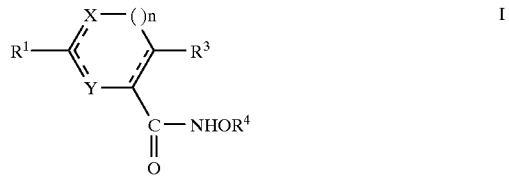

or a pharmaceutically acceptable salt thereof wherein:

$R^1$ represents $C_1$–$C_{12}$ alkyl, aryl$C_1$–$C_{12}$alkyl and aryl, wherein the alkyl group is substituted with 1–5 fluorines (1–3 fluorines with C1 alkyl) or 1–2 $OR^2$ groups, and aryl is selected from the group consisting of: phenyl, napthyl, indolyl, biphenyl, phenoxyphenyl, furanyl, thiophenyl and bithienyl, said aryl group is substituted by 1–2 groups of methylenedioxy attached to adjacent carbons, or 2–3 groups selected from $R^5$;

$R^2$ represents hydrogen, $C_1$–$C_6$ lower alkyl, phenyl or benzyl;

one of X and Y represents $N(R^2)_{0-1}$, and the other represents O;

dotted lines represent optional bonds;

$R^3$ represents H or $C_1$–$C_6$ lower alkyl optionally substituted by 1–3 groups selected from $OR^2$, $CO_2R^2$ or $N(R^2)_2$;

$R^4$ represents CO $C_1$–$C_6$ alkyl or CO phenyl and the alkyl and phenyl groups may be optionally substituted by 1–3 $R^2$, $CO_2R^2$ or $N(R^2)(R^2)$;

$R^5$ represents $C_1$–$C_6$ lower alkyl, $C_1$–$C_6$ lower alkoxy, halogen belonging to the group consisting of fluorine, bromine and chlorine, trifluoromethyl, $N(R^2)_2$, $N(R^2)(COR^4)$, phenoxy, $CO_2R^2$, hydroxy, $SO_2R^2$, $CON(R^2)(R^2)$ $OCOR^4$ and aryl lower alkoxy wherein the phenoxy and aryl lower alkoxy groups may be substituted by 1–2 groups selected from tert-butyl and iodine or 1–3 groups selected from $C_1$–$C_6$ lower alkyl, $C_1$–$C_6$ lower alkoxy, halogen, belonging to the group consisting of fluorine, bromine and chlorine, trifluoromethyl and hydroxy; and when no R⁵ group is present, and R³ represents H, the stereochemistry at the carbon atom bearing the group —C(O)—NHOR⁴ is (R); and n represents O.

2. A compound represented by formula Ia:

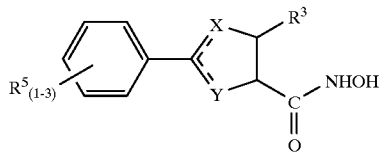

Ia wherein:
one of X and Y represent $N(R^2)_{0-1}$, and the other represents,

R² represents hydrogen or $C_1$–$C_6$ lower alkyl;

dotted lines represent an optional bond at the X or Y position;

R³ represents H or $C_1$–$C_6$ lower alkyl optionally substituted by OR², $CO_2R^2$ or $N(R^2)(R^2)$;

R⁵ represents $C_1$–$C_6$ lower alkyl, $C_1$–$C_6$ lower alkoxy, halogen, trifluoromethyl, methylenedioxy, $N(R^2)_2$, phenoxy, $CO_2R^2$, hydroxy, $R^2SO_2$, $CON(R^2)_2$ and benzyloxy wherein the phenoxy and benzyloxy groups may be substituted by $C_1$–$C_6$ lower alkyl, $C_1$–$C_6$ lower alkoxy, halogen, trifluoromethyl and hydroxy; and pharmaceutically acceptable salts and individual diastereomers thereof.

3. A compound in accordance with claim 2 represented by formula Ib:

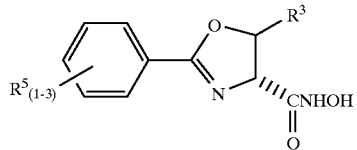

Ib wherein:
R³ represents hydrogen or $C_1$–$C_6$ lower alkyl optionally substituted by OR² or $N(R^2)_2$;

R² represents hydrogen or $C_1$–$C_6$ lower alkyl;

R⁵ represents $C_1$–$C_6$ lower alkyl, $C_1$–$C_6$ lower alkoxy, halogen, trifluoromethyl, methylenedioxy, phenoxy, hydroxy and benzyloxy, wherein the benzyloxy and phenoxy groups may be substituted by $C_1$–$C_6$ lower alkyl, $C_1$–$C_6$ lower alkoxy, halogen, trifluoromethyl and hydroxy groups;

and the pharmaceutically acceptable salts and individual diastereomers thereof.

4. A compound in accordance with claim 2 represented by the formula:

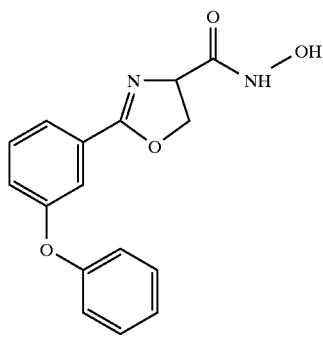

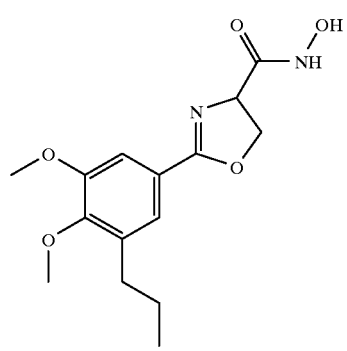

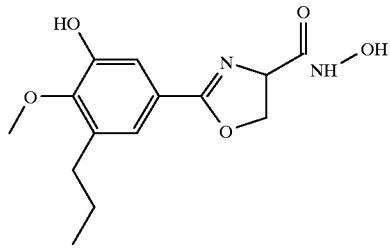

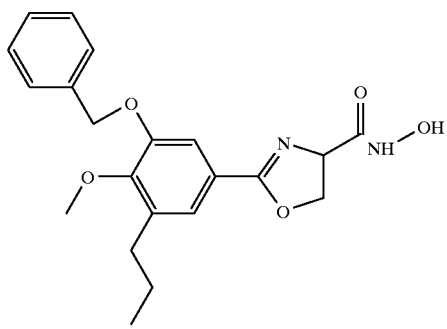

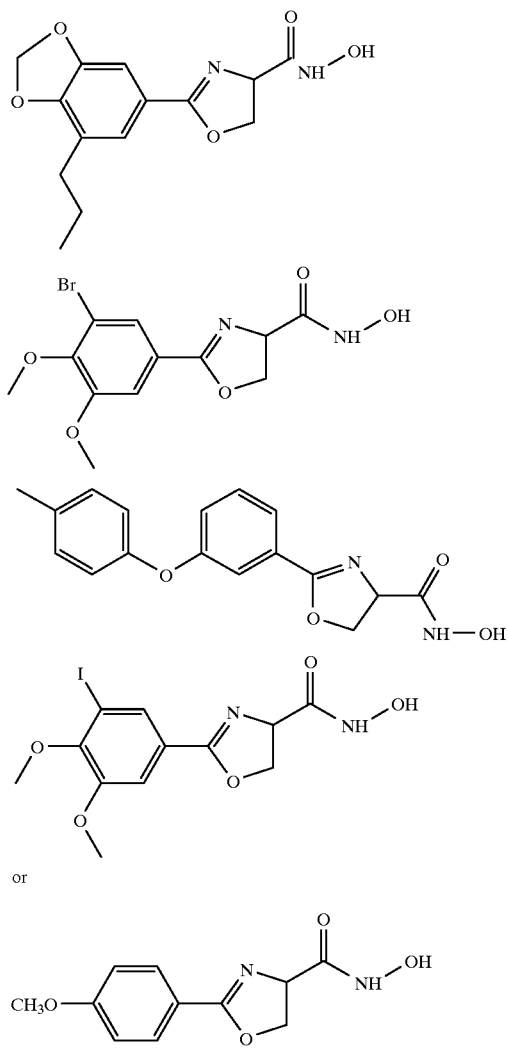
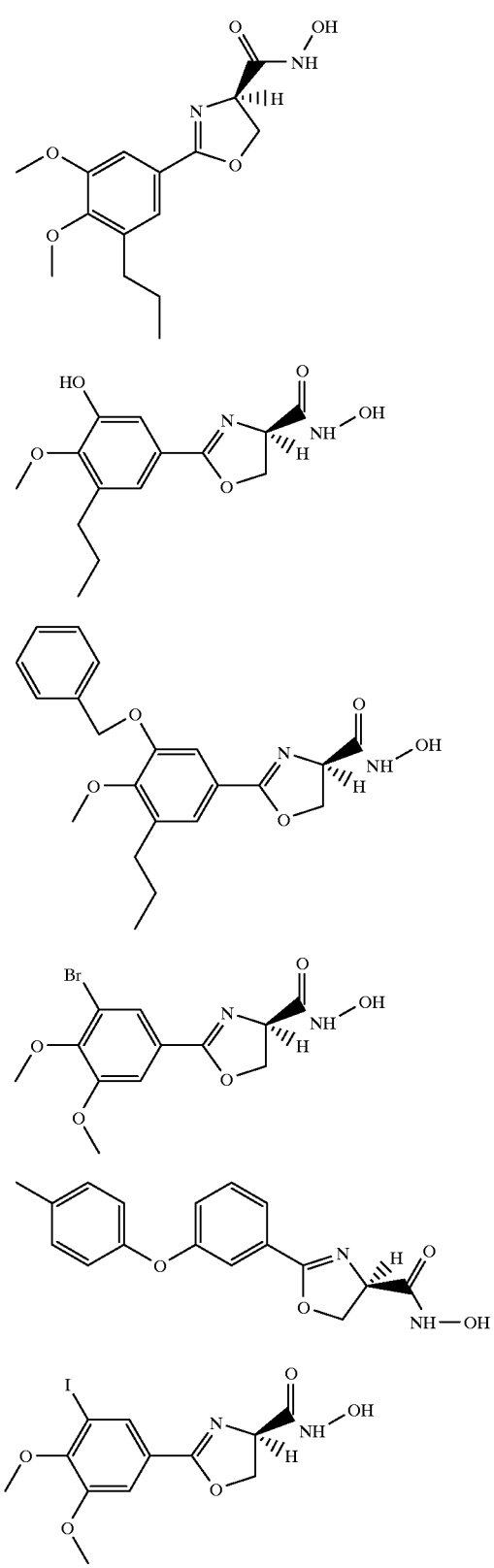
or a pharmaceutically acceptable salt or individual diastereomer thereof.
5. A compound in accordance with claim 2 represented by one of the following structures:
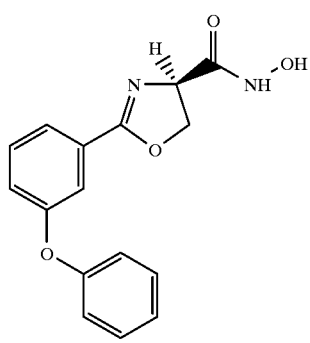

-continued

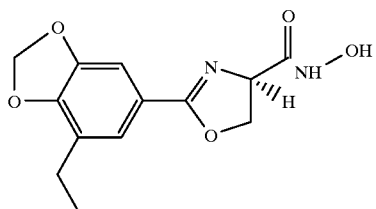

or

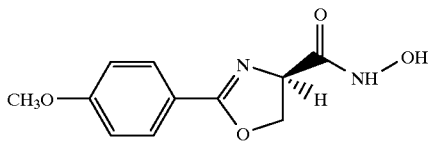

or a pharmaceutically acceptable salt thereof.

6. A compound in accordance with claim 2 represented by the formula:

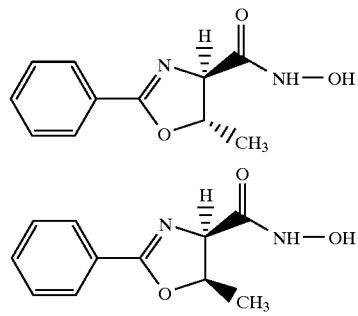

or a pharmaceutically acceptable salt thereof.

7. A compound falling within Table 1 below:

TABLE 1

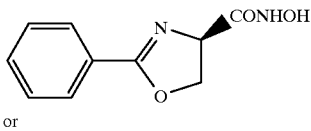

| entry | R |
|---|---|
| 1 | n-heptyl |
| 2 | t-butyl |
| 3 | m-tolyl |
| 4 | p-tolyl. |

8. A compound falling within Table 2:

TABLE 2

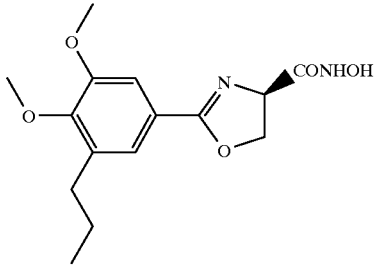

| entry | R |
|---|---|
| 1 | o-tolyl |
| 2 | 4-ethylphenyl |

TABLE 2-continued

| entry | R |
|---|---|
| 3 | 4-propylphenyl |
| 4 | 4-biphenyl |
| 5 | 3,4-dimethoxyphenyl |
| 6 | 3,4,5-trimethoxyphenyl |
| 7 | 2-furyl. |

9. A compound represented by the formula:

or a pharmaceutically acceptable salt thereof.

10. A pharmaceutical composition comprised of a compound as described in claim 1 in combination with a pharmaceutically acceptable carrier.

11. A pharmaceutical composition in accordance with claim 10 further comprised of a second antibacterial agent.

12. A pharmaceutical composition in accordance with claim 11 wherein the second antibacterial agent is selected from the group consisting of macrolides, beta lactams, quinolones, antibacterial sulfonamides and rifampicin.

13. A pharmaceutical composition in accordance with claim 12 wherein the second antibacterial agent is a macrolide antibiotic.

14. A pharmaceutical composition made by combining a compound as described in claim 1 with a pharmaceutically acceptable carrier.

15. A method of treating a bacterial infection in a mammalian patient in need of such treatment comprised of administering to said patient an antibacterially effective amount of a compound as described in claim 1.

16. A method of treating a bacterial infection in a mammalian patient in need of such treatment comprised of administering an antibacterially effective amount of a compound in accordance with claim 1 in combination with a second antibacterial agent.

17. A method in accordance with claim 16 wherein the second antibacterial agent is a macrolide antibiotic.

18. A method in accordance with claim 15 wherein the second antibacterial agent is selected from azithromycin, bacitracin and rifampicin.

* * * * *